US008101407B2

(12) United States Patent
Rudnicki et al.

(10) Patent No.: US 8,101,407 B2
(45) Date of Patent: Jan. 24, 2012

(54) STEM CELLS, NUCLEOTIDE SEQUENCES AND PROTEINS THEREFROM

(75) Inventors: Michael A. Rudnicki, Ottawa (CA); Shihuan Kuang, Ottawa (CA); Chet Holterman, Embrun (CA)

(73) Assignee: Ottawa Health Research Institute, Ottawa (CA)

( * ) Notice: Subject to any disclaimer, the term of this patent is extended or adjusted under 35 U.S.C. 154(b) by 450 days.

(21) Appl. No.: 12/094,585

(22) PCT Filed: Nov. 22, 2006

(86) PCT No.: PCT/CA2006/001907
§ 371 (c)(1),
(2), (4) Date: Sep. 11, 2008

(87) PCT Pub. No.: WO2007/059612
PCT Pub. Date: May 31, 2007

(65) Prior Publication Data
US 2009/0074730 A1    Mar. 19, 2009

(30) Foreign Application Priority Data

Nov. 22, 2005   (CA) .................................. 2524619

(51) Int. Cl.
*C12N 5/00*     (2006.01)
*C12N 5/07*     (2006.01)
(52) U.S. Cl. .................. 435/325; 435/320.1; 435/363; 435/455
(58) Field of Classification Search .................. 435/325, 435/320.1, 347, 363, 455
See application file for complete search history.

(56) References Cited

U.S. PATENT DOCUMENTS

| 4,405,712 | A | 9/1983 | Vande Woude et al. | 435/5 |
| 4,650,764 | A | 3/1987 | Temin et al. | 435/240 |
| 5,252,479 | A | 10/1993 | Srivastava | 435/235.1 |
| 5,501,979 | A | 3/1996 | Geller et al. | 435/320.1 |
| 5,506,138 | A | 4/1996 | Gelboin et al. | 435/252.3 |
| 5,561,063 | A | 10/1996 | Hock et al. | 435/320.1 |
| 5,604,090 | A | 2/1997 | Alexander et al. | 435/5 |
| 5,646,013 | A | 7/1997 | Takano et al. | 435/69.1 |
| 5,674,703 | A | 10/1997 | Woo et al. | 435/69.1 |
| 5,693,508 | A | 12/1997 | Chang | 435/172.3 |
| 5,700,470 | A | 12/1997 | Saito et al. | 424/233.1 |
| 5,719,054 | A | 2/1998 | Boursnell et al. | 435/320.1 |
| 5,731,172 | A | 3/1998 | Saito et al. | 435/91.42 |
| 5,739,018 | A | 4/1998 | Miyanohara et al. | 435/172.3 |

FOREIGN PATENT DOCUMENTS

| WO | WO 89/05345 | 6/1989 |
| WO | WO 90/06997 | 6/1990 |
| WO | WO 92/05266 | 4/1992 |
| WO | WO 92/07573 | 5/1992 |
| WO | WO 92/14829 | 9/1992 |

OTHER PUBLICATIONS

Relaix et al., A Pax3/Pax7-dependent population of skeletal muscle progenitor cells Nature 435, 948-953 (Jun. 16, 2005).*
Kochanek S, et al., Proc Natl Acad Sci U S A. Jun. 11, 1996;93(12):5731-6. A new adenoviral vector: Replacement of all viral coding sequences with 28 kb of DNA independently expressing both full-length dystrophin and beta-galactosidase.*
Schäfer BW, et al Nucleic Acids Res. Nov. 11, 1994;22(22):4574-82. Molecular cloning and characterization of a human PAX-7 cDNA expressed in normal and neoplastic myocytes.*
Blanco-Bose et al., 2001 W.E. Blanco-Bose, C.C. Yao, R.H. Kramer and H.M. Blau, Purification of mouse primary myoblasts based on alpha 7 integrin expression, Exp. Cell Res. 265 (2001), pp. 212-220.*
International Search Report PCT/CA2006/001907 Dated Mar. 9, 2007.
Kassar-Duchossoy, L. et al. Pax3/Pax7 Mark A Novel Population Of Primitive Myogenic Cells During Development Genes Dev. Jun. 15, 2005, vol. 19, pp. 1426-1431, ISSN 0890-9369.
Buckingham, M. et al. The formation of Skeletal Muscle: From Somite To Limb J. Anat. 2003, vol. 202, pp. 59-68, ISSN 0021-8782.
Holterman, C.E. et al. Molecular Regulation Of Satellite Function. Semin Cell Dev. Biol. Aug. 10, 2005, vol. 16, Nos. 4-5, pp. 575-584.
Polesskaya, A. et al. Stem Cells In Skeletal Muscle In Adult Stem Cells Edited By K. Turksen, Totowa, New Jersey: Humana Press Inc., 2004, pp. 37-50 ISBN 1-58829-152-9.
Katayama, S. et al. Antisense Transcription In The Mammalian Transcriptome Science. Sep. 2, 2005, vol. 309, No. 5740, pp. 1564-1566, ISSN 0036-8075.
GenBank Accession No. NM_001001979 (Oct. 8, 2005).
GenBank Accession No. NP_001001979 (Oct. 8, 2005).
Seale, P. et al. Pax7 Is Required For The Specification Of Myogenic Satellite Cells. Cell. Sep. 15, 2000, vol. 102 pp. 777-786, ISSN 0092-8674.
Beauchamp, J.R. et al. Expression of CD34 and Myf5 Defines The Majority Of Quiescent Adult Skeletal Muscle Satellite Cells. J. Cell Biol. 2000, vol. 151, No. 6, pp. 1221-1233, ISSN 0021-9525.
Richard Bischoff et al., "The Satellite Cell and Muscle Regeneration", Chapter 3, Part 1. The Scientific Basis of Myology, pp. 97-118 ((1994).
O. Armand et al, "Origin of Satellite Cells In Avian Skeletal Muscles", Archives d' Anatomie microscopique, Tome 72, No. 2, pp. 163-181 (1983).
Atsushi Asakura et al., "Myogenic Specification Of Side Population Cells In Skeletal Muscle", Article, The Journal of Cell Biology, vol. 159, No. 1, pp. 123-134 (2002). Jonathan R. Beauchamp et al., "Dynamics of Myoblast Transplantation Reveal a Discrete Minority of Precursors with Stem Cell—like Properties as the Myogenic Source", The Journal of Cell Biology, vol. 144, No. 6, pp. 1113-1121 (1999).
Raz Ben-Yair et al., "Lineage Analysis Of The Avian Dermomyotome Sheet Reveals The Existence Of Single Cells With Both Dermal And Muscle Progenitor", Research Article, Development, vol. 132, No. 4, pp. 689-701(2004).
Antje Bornemann et al, "Immunocytochemistry of M-Cadherin in Mature and Regenerating Rat Muscle", The Anatomical Record, vol. 239, pp. 119-125 (1994).

(Continued)

*Primary Examiner* — Maria Leavitt

(57) ABSTRACT

The present invention provides novel stem cells, nucleotide sequences and proteins therefrom. More specifically, the present invention provides Pax7+/Myf5− stem cells and methods for identifying and isolating them. Also provided is a MEGF10 nucleotide sequence and protein.

13 Claims, 14 Drawing Sheets

OTHER PUBLICATIONS

Dean J. Burkin et al., "The α7β1 Integrin In Muscle Development And Disease", Cell Tissue Res., vol. 296, pp. 183-190 (1999).

Ana Carmena et al., "*Inscuteable* And *Numb* Mediate Asymmetric Muscle Progenitor Cell Divisions During Drosophila?Myogenesis", Genes & Development, vol. 12, pp. 304-315 (1998).

Sophie B. P. Charge et al., "Cellular and Molecular Regulation of Muscle Regeneration", Physiol Rev., vol. 84, pp. 209-238, (2004).

Charlotte A. Collins et al., "Stem Cell Function, Self-Renewal, And Behavioral Heterogeneity of Cells From The Adult Muscle Satellite Cell Niche", Cell, vol. 122, pp. 289-301, (2005).

Ginetta Collo et al., "A New Isoform of the Laminin Receptor Integrin 60 7β1 Is Developmentally Regulated in Skeletal Muscle", The Journal Of Biological Chemistry, vol. 268, No. 25, pp. 19019-19024, (1993).

Irina M. Conboy et al., "The Regulation of Notch Signaling Controls Satellite Cell Activation And Cell Fate Determination In Postnatal Myogenesis", Developmental Cell, vol. 3, pp. 397-409, (2002).

D. D. W. Cornelison et al., "Single-Cell Analysis of Regulatory Gene Expression in Quiescent And Activated Mouse Skeletal Muscle Satellite Cells", Article No. DB978721, Developmental Biology, vol. 191, pp. 270-283 (1997).

D. D. W. Cornelison et al., "Syndecan-3 and Syndecan-4 Specifically Mark Skeletal Muscle Satellite Cells and Are Implicated In Satellite Cell Maintenance And Muscle Regeneration", Developmental Biology, vol. 239, pp. 79-94 (2001).

Joanne C. Cousins et al., "Regeneration Of Skeletal Muscle From Transplanted Immortalised Myoblasts Is Oligoclonal", Journal of Cell Science, vol. 117, pp. 3259-3269 (2004).

Luciana De Angelis et al., "Skeletal Myogenic Progenitors Originating From Embryonic Dorsal Aorta Coexpress Endothelial And Myogenic Markers And Contribute To Postnatal Muscle Growth And Regeneration", The Journal of Cell Biology, vol. 147, No. 4, pp. 869-877 (1999).

Marie-Claire Delfini et al., "Delta 1-Activated Notch Inhibits Muscle Differentiation Without Affecting Myf5 And Pax3 Expression In Chick Limb Myogenesis", Development, vol. 127, pp. 5213-5224 (2000).

Jyotsna Dhawan et al., "Stem Cells In Postnatal Myogenesis:Molecular Mechanisms Of Satellite Cell Quiescence, Activation And Replenishment", TRENDS in Cell Biology vol. 15, No. 12, pp. 666-673 (2005).

E. El Fahime et al, "Tubulyzine®, A Novel Tri-Substituted Triazine, Prevents The Early Cell Death Of Transplanted Myogenic Cells And Improves Transplantation Success", Biochem. Cell Biol., vol. 81, pp. 81-90 (2003).

Ying Fan et al., "Rapid Death Of Injected Myoblasts In Myoblast Transfer Therapy", Muscle & Nerve, vol. 19, pp. 853-860 (1996).

Elaine Fuchs et al., "Socializing with the Neighbors: Stem Cells and Their Niche", Review, Cell, vol. 116, pp. 769-778, (2004).

Daniel J. Garry et al., "Persistent Expression Of MNF Identifies Myogenic Stem Cells In Postnatal Muscles", Developmental Biology, Article No. DB978657., vol. 188, pp. 280-294 (1997).

Jérôme Gros et al., "A Common Somitic Origin For Embryonic Muscle Progenitors And Satellite Cells", Letters, Nature ,vol. 435, No. 16, pp. 954-958 (2005).

L. Heslop et al., "Research Article, Transplanted Primary Neonatal Myoblasts Can Give Rise To Functional Satellite Cells As Identified Using The Myf5$^{nlacZ/+}$ Mouse", Gene Therapy, vol. 8, pp. 778-783 (2001).

L. Heslop et al., "Evidence For A Myogenic Stem Cell That Is Exhausted In Dystrophic Muscle", Journal of Cell Science, vol. 113, pp. 2299-2308 (2000).

I. Kinoshita et al., "Immunosuppression With FK 506 Insures Good Success Of Myoblast Transplantation In MDX Mice", Transplantation Proceedings, vol. 26, No. 6, pp. 3518 (1994).

Stuart I. Hodgetts et al., "Why Do Cultured Transplanted Myoblasts Die In Vivo? DNA Quantification Shows Enhanced Survival of Donor Male Myoblasts In Host Mice Depleted Of CD4$^+$ and CD8$^+$ Cells or NK1.1$^+$ Cells", Cell Transplantation, vol. 9, pp. 489-502, (2000).

Tamara Holowacz et al., "Asymmetric Localization Of Numb In The Chick Somite and the Influence Of Myogenic Signals", Research Article, Developmental Dynamics, vol. 235, pp. 633-645, (2006).

A Irintchev et al., "Expression Pattern Of M-Cadherin In Normal, Denervated, And Regenerating Mouse Muscles" Developmental Dynamics, vol. 199, pp. 326-337 (1994).

Shihuan Kuang et al "Distinct Roles For Pax7 and Pax3 In Adult Regenerative Myogenesis", The JCB: Article, Journal of Cell Biology, vol. 172, No. 1, pp. 103-113 (2006).

Mark A. LaBarge et al., "Biological Progression From Adult Bone Marrow To Mononucleate Muscle Stem Cell To Multinucleate Muscle Fiber In Response To Injury", Cell, vol. 111, pp. 589-601, (2002).

Terry Lechler et al., "Asymmetric Cell Divisions Promote Stratification And Differentiation Of Mammalian Skin", Letters, Nature, vol. 437, No. 8, pp. 275-280, (2005).

Alexander Mauro, "Satellite Cell Of Skeletal Muscle Fibers", Rockefeller Institute, Brief Notes, pp. 493-494 and 1 page photograph (1961).

Lynn A. Megeney et al., "MyoD Is Required For Myogenic Stem Cell Function In Adult Skeletal Muscle", Gene & Development, vol. 10, pp. 1173-1183 (1996).

Shigeru Minoguchi et al., "RBP-L, A Transcription Factor Related to RBP-Jk", Molecular And Cellular Biology, vol. 17, No. 5, pp. 2679-2687 (1997).

Didier Montarras et al., "Direct Isolation Of Satellite Cells For Skeletal Muscle Regeneration", Reports, Science,, vol. 309, pp. 2064-2067 (2005).

Hugo C. Olguin et al., "Pax-7 Up-Regulation Inhibits Myogenesis And Cell Cycle Progression In Satellite Cells: A Potential Mechanism For Self-Renewal", Developmental Biology, vol. 275, pp. 375-388 (2004).

Svetlana Oustanina et al., "Pax7 Directs Postnatal Renewal And Propagation Of Myogenic Satellite Cells But Not Their Specification", The EMBO Journal, vol. 23, pp. 3430-3439, (2004).

Anna Polesskaya et al., "Wnt Signaling Induces The Myogenic Specification Of Resident CD45$^+$ Adult Stem Cells During Muscle Regeneration", Cell, vol. 113, pp. 841-852, (2003).

Zhuqing Qu et al., "Development Of Approaches To Improve Cell Survival In Myoblast Transfer Therapy", The Journal of Cell Biology, vol. 142, No. 5, pp. 1257-1267 (1998).

Thomas A. Rando et al., "Primary Mouse Myoblast Purification, Characterization, And Transplantation for Cell-Mediated Gene Therapy", The Journal of Cell Biology, vol. 125, No. 6, pp. 1275-1287 (1994).

Frédéric Relaix et al., "Pax3 And Pax7 Have Distinct And Overlapping Functions In Adult Muscle Progenitor Cells", The Journal of Cell Biology, vol. 172, No. 1, pp. 91-102 (2006).

Glenn D. Rosen et al., "Roles for the Integrin VLA-4 And Its Counter Receptor VCAM-1 in Myogenesis", Cell, vol. 69, pp. 1107-1119, (1992).

J. David Rosenblatt et al., "Culturing Satellite Cells From Living Single Muscle Fiber Explants", In Vitro Cell. Dev. Biol.-Animal, vol. 31, pp. 773-779, (1995).

Jaclyn Schienda et al., "Somitic Origin Of Limb Muscle Satellite And Side Population Cells", PNAS vol. 103, No. 4, pp. 945-950 (2006).

Edward Schultz, "Satellite Cell Proliferative Compartments In Growing Skeletal Muscles", Developmental Biology, Article No. 0097, vol. 175, pp. 84-94 (1996).

Shankar Srinivas et al., "Cre Reporter Strains Produced By Targeted Insertion Of EYFP And ECFP Into The ROSA26 Locus", Methodology Article, BMC Developmental Biology, vol. 1, No. 4, 8 pages (2001).

S. Tajbakhsh et al., "Gene Targeting The *myf*-5 Locus With *nlacZ* Reveals Expression Of This Myogenic Factor In Mature Skeletal Muscle Fibres As Well As Early Embryonic Muscle", Developmental Dynamics, vol. 206, pp. 291-300 (1996).

Michelle D. Tallquist et al., "Early Myotome Specification Regulates PDGFA Expression And Axial Skeleton Development", Development, vol. 127, pp. 5059-5070 (2000).

Sara J. Venters et al., "Asymmetric Cell Divisions Are Concentrated In The Dermomyotome Dorsomedial Lip During Epaxial Primary Myotome Morphogenesis", Anat. Embryol., vol. 209, pp. 449-460, (2005).

Zipora Yablonka-Reuveni et al., "Satellite Cells From Dystrophic (Mdx) Mice Display Accelerated Differentiation In Primary Cultures And In Isolated Myofibers", Developmental Dynamics, vol. 235, pp. 203-212, (2006).

Peter S. Zammit et al., "Muscle Satellite Cells Adopt Divergent Fates: A Mechanism For Self-Renewal?", Article, The Journal of Cell Biology, vol. 166, No. 3, pp. 347-357 (2004).

Peter S. Zammit et al., "Pax7 And Myogenic Progression In Skeletal Muscle", Research Article, Journal of Cell Science, vol. 119, pp. 1824-1832 (2006).

Branko V. Latinkić et al., The *Xenopus Brachyury* Promoter Is Activated By FGF And Low Concentrations Of Activin and Suppressed By High Concentrations Of Activin And By Paired-Type Homeodomain Proteins, Errata, Genes & Development, vol. 11:, pp. 3265-3276 (1997).

\* cited by examiner

SEQUENCE LISTING

```
<160> NUMBER OF SEQ ID NOS: 22

<210> SEQ ID NO 1
<211> LENGTH: 1146
<212> TYPE: PRT
<213> ORGANISM: mus musculus
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid

<400> SEQUENCE: 1

Met Ala Ile Ser Ser Ser Ser Cys Leu Gly Leu Ile Cys Ser Leu Leu
1               5                   10                  15

Cys His Trp Val Gly Thr Ala Ser Ser Leu Asn Leu Glu Asp Pro Asn
            20                  25                  30

Val Cys Ser His Trp Glu Ser Tyr Ser Val Thr Val Gln Glu Ser Tyr
        35                  40                  45

Pro His Pro Phe Asp Gln Ile Tyr Tyr Thr Ser Cys Thr Asp Ile Leu
    50                  55                  60

Asn Trp Phe Lys Cys Thr Arg His Arg Ile Ser Tyr Arg Thr Ala Tyr
65                  70                  75                  80

Arg His Gly Glu Lys Thr Met Tyr Arg Arg Lys Ser Gln Cys Cys Pro
                85                  90                  95

Gly Phe Tyr Glu Ser Arg Asp Met Cys Val Pro His Cys Ala Asp Lys
            100                 105                 110

Cys Val His Gly Arg Cys Ile Ala Pro Asn Thr Cys Gln Cys Glu Pro
        115                 120                 125

Gly Trp Gly Gly Thr Asn Cys Ser Ser Ala Cys Asp Gly Asp His Trp
```

```
               130                 135                 140
Gly Pro His Cys Ser Ser Arg Cys Gln Cys Lys Asn Arg Ala Leu Cys
145                 150                 155                 160

Asn Pro Ile Thr Gly Ala Cys His Cys Ala Ala Gly Tyr Arg Gly Trp
                165                 170                 175

Arg Cys Glu Asp Arg Cys Glu Gln Gly Thr Tyr Gly Asn Asp Cys His
            180                 185                 190

Gln Arg Cys Gln Arg Gln Asn Gly Ala Thr Cys Asp His Ile Thr Gly
        195                 200                 205

Glu Cys Arg Cys Ser Pro Gly Tyr Thr Gly Ala Phe Cys Glu Asp Leu
210                 215                 220

Cys Pro Pro Gly Lys His Gly Pro His Cys Glu Gln Arg Cys Pro Cys
225                 230                 235                 240

Gln Asn Gly Gly Val Cys His His Val Thr Gly Glu Cys Ser Cys Pro
                245                 250                 255

Ser Gly Trp Met Gly Thr Val Cys Gly Gln Pro Cys Pro Glu Gly Arg
            260                 265                 270

Phe Gly Lys Asn Cys Ser Gln Glu Cys Gln Cys His Asn Gly Gly Thr
        275                 280                 285

Cys Asp Ala Ala Thr Gly Gln Cys His Cys Ser Pro Gly Tyr Thr Gly
290                 295                 300

Glu Arg Cys Gln Asp Glu Cys Pro Val Gly Ser Tyr Gly Val Arg Cys
305                 310                 315                 320

Ala Glu Ala Cys Arg Cys Val Asn Gly Gly Lys Cys Tyr His Val Ser
                325                 330                 335

Gly Thr Cys Leu Cys Glu Ala Gly Phe Ser Gly Glu Leu Cys Glu Ala
            340                 345                 350

Arg Leu Cys Pro Glu Gly Leu Tyr Gly Ile Lys Cys Asp Lys Arg Cys
        355                 360                 365

Pro Cys His Leu Asp Asn Thr His Ser Cys His Pro Met Ser Gly Glu
370                 375                 380

Cys Gly Cys Lys Pro Gly Trp Ser Gly Leu Tyr Cys Asn Glu Thr Cys
385                 390                 395                 400

Ser Pro Gly Phe Tyr Gly Glu Ala Cys Gln Gln Ile Cys Ser Cys Gln
                405                 410                 415

Asn Gly Ala Asp Cys Asp Ser Val Thr Gly Arg Cys Ala Cys Ala Pro
            420                 425                 430

Gly Phe Lys Gly Thr Asp Cys Ser Thr Pro Cys Pro Leu Gly Arg Tyr
        435                 440                 445

Gly Ile Asn Cys Ser Ser Arg Cys Gly Cys Lys Asn Asp Ala Val Cys
450                 455                 460

Ser Pro Val Asp Gly Ser Cys Ile Cys Lys Ala Gly Trp His Gly Val
465                 470                 475                 480

Asp Cys Ser Ile Arg Cys Pro Ser Gly Thr Trp Gly Phe Gly Cys Asn
                485                 490                 495

Leu Thr Cys Gln Cys Leu Asn Gly Gly Ala Cys Asn Thr Leu Asp Gly
            500                 505                 510

Thr Cys Thr Cys Ala Pro Gly Trp Arg Gly Ala Lys Cys Glu Phe Pro
        515                 520                 525

Cys Gln Asp Gly Thr Tyr Gly Leu Asn Cys Ala Glu Arg Cys Asp Cys
530                 535                 540

Ser His Ala Asp Gly Cys His Pro Thr Thr Gly His Cys Arg Cys Leu
545                 550                 555                 560
```

-continued

```
Pro Gly Trp Ser Gly Val His Cys Asp Ser Val Cys Ala Glu Gly Arg
            565                 570                 575

Trp Gly Pro Asn Cys Ser Leu Pro Cys Tyr Cys Lys Asn Xaa Ala Ser
            580                 585                 590

Cys Ser Pro Asp Xaa Gly Ile Cys Glu Cys Ala Pro Gly Phe Arg Gly
            595                 600                 605

Thr Thr Cys Gln Arg Ile Cys Ser Pro Gly Phe Tyr Gly His Arg Cys
            610                 615                 620

Ser Gln Thr Cys Pro Gln Cys Val His Ser Ser Gly Pro Cys His His
625                 630                 635                 640

Ile Thr Gly Leu Cys Asp Cys Leu Pro Phe Phe Thr Gly Ala Leu Cys
            645                 650                 655

Asn Glu Val Cys Pro Ser Gly Arg Phe Gly Lys Asn Cys Ala Gly Val
            660                 665                 670

Cys Thr Cys Thr Asn Asn Gly Thr Cys Asn Pro Ile Asp Arg Ser Cys
            675                 680                 685

Gln Cys Tyr Pro Gly Trp Ile Gly Ser Asp Cys Ser Gln Pro Cys Pro
            690                 695                 700

Pro Ala His Trp Gly Pro Asn Cys Ile His Thr Cys Asn Cys His Asn
705                 710                 715                 720

Gly Ala Phe Cys Ser Ala Tyr Asp Gly Glu Cys Lys Cys Thr Pro Gly
            725                 730                 735

Trp Thr Gly Leu Tyr Cys Thr Gln Arg Cys Pro Leu Gly Phe Tyr Gly
            740                 745                 750

Lys Asp Cys Ala Leu Ile Cys Gln Cys Gln Asn Gly Ala Asp Cys Asp
            755                 760                 765

His Ile Ser Gly Gln Cys Thr Cys Arg Thr Gly Phe Met Gly Arg His
            770                 775                 780

Cys Glu Gln Lys Cys Pro Ala Gly Thr Tyr Gly Tyr Gly Cys Arg Gln
785                 790                 795                 800

Ile Cys Asp Cys Leu Asn Asn Ser Thr Cys Asp His Ile Thr Gly Thr
            805                 810                 815

Cys Tyr Cys Ser Pro Gly Trp Lys Gly Ala Arg Cys Asp Gln Ala Gly
            820                 825                 830

Val Ile Ile Val Gly Asn Leu Asn Ser Leu Ser Arg Thr Ser Thr Ala
            835                 840                 845

Leu Pro Ala Asp Ser Tyr Gln Ile Gly Ala Ile Ala Gly Ile Val Val
850                 855                 860

Leu Val Leu Val Val Leu Phe Leu Leu Ala Leu Phe Ile Ile Tyr Arg
865                 870                 875                 880

His Lys Gln Lys Arg Lys Glu Ser Ser Met Pro Ala Val Thr Tyr Thr
            885                 890                 895

Pro Ala Met Arg Val Ile Asn Ala Asp Tyr Thr Ile Ala Glu Thr Leu
            900                 905                 910

Pro His Ser Asn Gly Gly Asn Ala Asn Ser His Tyr Phe Thr Asn Pro
            915                 920                 925

Ser Tyr His Thr Leu Ser Gln Cys Ala Thr Ser Pro His Val Asn Asn
            930                 935                 940

Arg Asp Arg Met Thr Ile Ala Lys Ser Lys Asn Asn Gln Leu Phe Val
945                 950                 955                 960

Asn Leu Lys Asn Val Asn Pro Gly Lys Arg Gly Thr Leu Val Asp Cys
            965                 970                 975

Thr Gly Thr Leu Pro Ala Asp Trp Lys Gln Gly Gly Tyr Leu Asn Glu
            980                 985                 990
```

| Leu | Gly | Ala | Phe | Gly | Leu | Asp | Arg | Ser | Tyr | Met | Gly | Lys | Ser | Leu | Lys |
| | | 995 | | | | | 1000 | | | | | 1005 | | | |

| Asp | Leu | Gly | Lys | Asn | Ser | Glu | Tyr | Asn | Ser | Ser | Thr | Cys | Ser | Leu |
| | 1010 | | | | | 1015 | | | | | 1020 | | | |

| Ser | Ser | Ser | Glu | Asn | Pro | Tyr | Ala | Thr | Ile | Lys | Asp | Pro | Pro | Ala |
| | 1025 | | | | | 1030 | | | | | 1035 | | | |

| Leu | Leu | Pro | Lys | Ser | Ser | Glu | Cys | Gly | Tyr | Val | Glu | Met | Lys | Ser |
| | 1040 | | | | | 1045 | | | | | 1050 | | | |

| Pro | Ala | Arg | Arg | Asp | Ser | Pro | Tyr | Ala | Glu | Ile | Asn | Asn | Ser | Thr |
| | 1055 | | | | | 1060 | | | | | 1065 | | | |

| Pro | Ala | Asn | Arg | Asn | Val | Tyr | Glu | Val | Glu | Pro | Thr | Val | Ser | Val |
| | 1070 | | | | | 1075 | | | | | 1080 | | | |

| Val | Gln | Gly | Val | Phe | Ser | Asn | Ser | Gly | His | Val | Thr | Gln | Asp | Pro |
| | 1085 | | | | | 1090 | | | | | 1095 | | | |

| Tyr | Asp | Leu | Pro | Lys | Asn | Ser | His | Ile | Pro | Cys | His | Tyr | Asp | Leu |
| | 1100 | | | | | 1105 | | | | | 1110 | | | |

| Leu | Pro | Val | Arg | Asp | Ser | Ser | Ser | Pro | Lys | Arg | Glu | Asp | Gly |
| | 1115 | | | | | 1120 | | | | | 1125 | | |

| Gly | Gly | Ser | Asn | Ser | Thr | Ser | Ser | Asn | Ser | Thr | Ser | Ser | Ser | Ser |
| | 1130 | | | | | 1135 | | | | | 1140 | | | |

Ser Ser Ser
    1145

<210> SEQ ID NO 2
<211> LENGTH: 3440
<212> TYPE: DNA
<213> ORGANISM: mus musculus

<400> SEQUENCE: 2

```
atggcgattt cttcaagttc gtgcctgggc ctcatctgct cactgctctg tcactgggtg     60
gggacagcat cctccctgaa cctggaagac cccaacgtat gcagccactg gaaaagctac    120
tcggtgactg tgcaggagtc gtatccacat cccttcgatc agatctacta cacaagctgc    180
accgacatcc tgaactggtt taaatgcaca cggcacagaa tcagctaccg acagcctac    240
cgccacgggg agaaaaccat gtatagacgc aaatcccagt gttgcccagg atttatgaa    300
agccgagaca tgtgtgtccc tcactgtgct gataaatgtg tccatggtcg ctgcattgct    360
ccaaacacct gtcagtgtga gcctggctgg ggtgggacca actgtagcag tgcttgtgat    420
ggtgatcact gggggcctca ctgcagcagc cgatgccagt gcaaaaacag agctttgtgt    480
aaccccatca ccggtgcttg ccactgcgct gcgggctacc ggggatggcg ctgcgaggac    540
cgttgtgaac agggcacgta cggtaacgac tgtcaccaaa gatgccagcg tcagaatggg    600
gcgacctgtg accacatcac tgggaatgc cgttgttcac ctgggtacac tggagccttc    660
tgtgaggatc tttgtcctcc tggcaaacat ggtccacatt gtgagcagag tgtccctgc    720
caaaatgggg gcgtgtgcca ccatgtcact ggagagtgct cttgcccttc tggttggatg    780
ggcacagtgt gtggtcagcc ctgccctgag gtcgctttg aaagaactg ttcccaagaa    840
tgccagtgtc acaatggagg aacgtgtgat gctgccacag gccagtgtca ctgcagccca    900
ggatacacag ggaacggtg tcaggacgaa tgtcctgttg ggagctatgg agttcgctgt    960
gctgaggcct gcaggtgtgt caacggaggg aagtgttacc acgtgagtgg cacatgcctg   1020
tgcgaagcag gcttttcggg tgaactttgc gaggcgcgcc tgtgtccgga ggggctttac   1080
ggcatcaaat gtgacaagcg gtgcccctgc acctggacaa cactcacag ctgtcatccc   1140
```

```
atgtctggag agtgtggctg caagccgggt tggtcgggac tgtactgtaa tgaaacatgc   1200 tccccctggat tctacgggga ggcttgccaa cagatctgca gctgccagaa cggggcggac   1260
tgcgacagtg tgactggaag gtgtgcctgc gctccaggat tcaaagggac tgactgctct   1320
actccgtgtc ctctgggacg ctacgggata aattgttctt ctcgctgtgg ctgtaaaaat   1380
gatgctgtct gttctcctgt ggatggatca tgtatctgta aggcaggctg gcacggggtg   1440
gactgttcca tccgctgccc cagtggcaca tggggctttg gctgtaacct aacgtgtcag   1500
tgcctcaatg gcggtgcctg caacacgctg gatgggacct gcacctgtgc gcccggatgg   1560
cgaggcgcga gtgtgaatt ccctgccag gatggcactt atgggctgaa ctgtgccgag   1620
cgctgtgact gcagccatgc agatggctgt cacccactagaa caggccattg ccgctgcctc   1680
cctggatggt caggtgtgca ctgtgacagt gtgtgcgctg agggacgctg gggtcctaac   1740
tgctcgctgc cctgctactg taaaaatrgr gcttcgtgtt ctccggatga wggcatctgt   1800
gagtgtgcac ccggattccg aggcaccact tgccagagaa tctgctcccc cggttttttat   1860 ggacatcgct gtagccagac ctgcccgcag tgtgtgcaca gcagtgggcc ctgccaccac   1920
atcacgggcc tgtgtgactg cttaccttc ttcaccggtg ccctgtgcaa tgaagtgtgt   1980
cccagtggca gatttgggaa aaactgtgca ggcgtttgta cttgcaccaa caatggcacc   2040
tgtaacccca tcgacagatc ctgccagtgt tacccaggct ggattggcag tgactgctcc   2100
cagccctgtc cacctgcgca ctggggtccg aactgcatcc acacctgcaa ctgccacaac   2160 ggagccttt gcagcgccta tgayggggaa tgcaaatgca ctcctggctg gacggggctc   2220
tactgcactc agagatgccc tctgggcttc tatggtaagg actgtgcact gatatgccaa   2280
tgtcaaaacg gagctgactg cgaccatatc tcggggcagt gtacctgccg cacgggattc   2340
atgggacggc actgtgaaca gaagtgccct gcgggaacat acggctatgg ctgtcgccag   2400
atctgtgact gtctgaacaa ctccacctgt gaccacatca ctggcacgtg ttactgtagc   2460
ccaggatgga aggggcacg atgtgaccaa gctggggtta tcatcgtggg caatctgaac   2520
agcttaagcc ggaccagcac cgcccttcct gccgattcct atcagatcgg ggccatcgcg   2580
ggcatcgtgg tcctcgttct tgttgtgctc ttcctgctgg cgctgttcat catctacaga   2640
cacaagcaga agaggaagga atcaagcatg ccggccgtga cctacacccc cgccatgagg   2700
gtcatcaatg cagactatac catcgcagaa accctgcctc acagcaatgg tggaaatgcc   2760
aacagccact actttaccaa tcccagttat cacacactta gccagtgtgc cacatcccct   2820
catgtgaaca ataggacag gatgaccatt gcaaagtcaa aaaacaatca gctgtttgtg   2880
aatcttaaaa atgtgaatcc agggaagaga gggacattgg tggactgcac tgggacattg   2940
ccagctgact ggaagcaagg aggctacctc aatgagcttg gtgctttcgg gctgacagaa   3000
agctacatgg gaaagtcctt aaaagatctg gggaagaact ctgaatataa ttcaagcact   3060
tgctccttaa gcagctctga aaacccatat gccaccatta agacccgcc tgcactcctg   3120 cctaaaagct ccgagtgcgg ctacgtggag atgaagtcgc cggcgcggag agactcccca   3180
tatgcagaga tcaacaactc aactccagcc aacaggaatg tctatgaagt cgaacctaca   3240
gtgagcgttg tgcaaggagt attcagcaac agcggtcacg tcacccaaga cccatatgac   3300
cttccaaaga acagtcacat cccttgccat tatgacctgc tgccagtaag ggacagttca   3360
tcctccccaa agagagagga tggtggtggc agcaacagca ccagcagcaa cagcaccagc   3420
agcagcagca gcagcagtga                                              3440
```

<210> SEQ ID NO 3

```
<211> LENGTH: 21
<212> TYPE: PRT
<213> ORGANISM: mus musculus

<400> SEQUENCE: 3

Gly Cys Thr Ala Cys Cys Ala Gly Thr Ala Cys Ala Gly Cys Cys Ala
1               5                   10                  15

Gly Thr Ala Thr Gly
            20

<210> SEQ ID NO 4
<211> LENGTH: 21
<212> TYPE: PRT
<213> ORGANISM: mus musculus

<400> SEQUENCE: 4

Gly Thr Cys Ala Cys Thr Ala Ala Gly Cys Ala Thr Gly Gly Gly Thr
1               5                   10                  15

Ala Gly Ala Thr Gly
            20

<210> SEQ ID NO 5
<211> LENGTH: 20
<212> TYPE: PRT
<213> ORGANISM: mus musculus

<400> SEQUENCE: 5

Thr Gly Ala Gly Gly Gly Ala Ala Cys Ala Gly Gly Thr Gly Gly Ala
1               5                   10                  15

Gly Ala Ala Cys
            20

<210> SEQ ID NO 6
<211> LENGTH: 20
<212> TYPE: PRT
<213> ORGANISM: mus musculus

<400> SEQUENCE: 6

Gly Cys Ala Ala Ala Ala Ala Gly Ala Ala Cys Ala Gly Gly Cys Ala
1               5                   10                  15

Gly Ala Gly Gly
            20

<210> SEQ ID NO 7
<211> LENGTH: 20
<212> TYPE: PRT
<213> ORGANISM: mus musculus

<400> SEQUENCE: 7

Cys Ala Ala Ala Cys Thr Cys Thr Thr Cys Gly Cys Gly Gly Thr Cys
1               5                   10                  15

Thr Thr Thr Cys
            20

<210> SEQ ID NO 8
<211> LENGTH: 18
<212> TYPE: PRT
<213> ORGANISM: mus musculus

<400> SEQUENCE: 8

Ala Ala Cys Ala Gly Cys Thr Cys Cys Thr Cys Gly Cys Cys Cys Thr
1               5                   10                  15

Thr Gly
```

```
<210> SEQ ID NO 9
<211> LENGTH: 23
<212> TYPE: PRT
<213> ORGANISM: mus musculus

<400> SEQUENCE: 9

Gly Cys Gly Gly Thr Cys Thr Gly Gly Cys Ala Gly Thr Ala Ala Ala
1               5                   10                  15

Ala Ala Cys Thr Ala Thr Cys
            20

<210> SEQ ID NO 10
<211> LENGTH: 23
<212> TYPE: PRT
<213> ORGANISM: mus musculus

<400> SEQUENCE: 10

Gly Thr Gly Ala Ala Cys Ala Gly Cys Ala Thr Thr Gly Cys Thr
1               5                   10                  15

Gly Thr Cys Ala Cys Thr Thr
            20

<210> SEQ ID NO 11
<211> LENGTH: 20
<212> TYPE: PRT
<213> ORGANISM: mus musculus

<400> SEQUENCE: 11

Ala Gly Cys Cys Ala Thr Gly Thr Ala Cys Gly Thr Ala Gly Cys Cys
1               5                   10                  15

Ala Thr Cys Cys
            20

<210> SEQ ID NO 12
<211> LENGTH: 20
<212> TYPE: PRT
<213> ORGANISM: mus musculus

<400> SEQUENCE: 12

Cys Thr Cys Thr Cys Ala Gly Cys Thr Gly Thr Gly Gly Thr Gly Gly
1               5                   10                  15

Thr Gly Ala Ala
            20

<210> SEQ ID NO 13
<211> LENGTH: 20
<212> TYPE: PRT
<213> ORGANISM: mus musculus

<400> SEQUENCE: 13

Thr Gly Ala Gly Ala Cys Thr Gly Cys Cys Ala Ala Gly Thr Gly
1               5                   10                  15

Thr Thr Gly Cys
            20

<210> SEQ ID NO 14
<211> LENGTH: 20
<212> TYPE: PRT
<213> ORGANISM: mus musculus

<400> SEQUENCE: 14

Gly Thr Gly Gly Gly Ala Gly Ala Cys Ala Gly Ala Gly Thr Gly Gly
```

```
                1               5                  10                 15

Gly Thr Gly Thr
            20

<210> SEQ ID NO 15
<211> LENGTH: 20
<212> TYPE: PRT
<213> ORGANISM: mus musculus

<400> SEQUENCE: 15

Gly Cys Ala Gly Gly Ala Gly Cys Ala Gly Gly Ala Gly Gly Thr Gly
1               5                  10                 15

Ala Thr Ala Gly
            20

<210> SEQ ID NO 16
<211> LENGTH: 20
<212> TYPE: PRT
<213> ORGANISM: mus musculus

<400> SEQUENCE: 16

Gly Cys Gly Thr Thr Thr Cys Thr Thr Gly Gly Ala Cys Thr Cys Thr
1               5                  10                 15

Cys Cys Ala Gly
            20

<210> SEQ ID NO 17
<211> LENGTH: 20
<212> TYPE: PRT
<213> ORGANISM: mus musculus

<400> SEQUENCE: 17

Gly Thr Cys Cys Ala Gly Ala Gly Gly Cys Cys Ala Ala Gly Ala Gly
1               5                  10                 15

Ala Cys Thr Gly
            20

<210> SEQ ID NO 18
<211> LENGTH: 20
<212> TYPE: PRT
<213> ORGANISM: mus musculus

<400> SEQUENCE: 18

Cys Ala Gly Ala Ala Gly Gly Ala Gly Gly Cys Cys Ala Gly Cys Ala
1               5                  10                 15

Thr Ala Ala Gly
            20

<210> SEQ ID NO 19
<211> LENGTH: 20
<212> TYPE: PRT
<213> ORGANISM: mus musculus

<400> SEQUENCE: 19

Cys Cys Gly Gly Cys Thr Gly Ala Ala Gly Cys Thr Ala Cys Ala Gly
1               5                  10                 15

Ala Ala Ala Cys
            20

<210> SEQ ID NO 20
<211> LENGTH: 20
<212> TYPE: PRT
<213> ORGANISM: mus musculus
```

```
<400> SEQUENCE: 20

Gly Ala Ala Ala Gly Thr Cys Cys Gly Cys Cys Thr Thr Cys Thr Thr
1               5                   10                  15

Gly Thr Thr Gly
            20

<210> SEQ ID NO 21
<211> LENGTH: 20
<212> TYPE: PRT
<213> ORGANISM: mus musculus

<400> SEQUENCE: 21

Cys Cys Gly Cys Ala Cys Thr Ala Gly Ala Ala Gly Cys Ala Ala
1               5                   10                  15

Gly Thr Cys Cys
            20

<210> SEQ ID NO 22
<211> LENGTH: 20
<212> TYPE: PRT
<213> ORGANISM: mus musculus

<400> SEQUENCE: 22

Ala Cys Ala Ala Ala Gly Thr Cys Cys Cys Thr Thr Thr Gly Cys
1               5                   10                  15

Thr Cys Cys Thr
            20
```

STEM CELLS, NUCLEOTIDE SEQUENCES AND PROTEINS THEREFROM

This application is a 371 filing of International Patent Application No. PCT/CA2006/001907, filed Nov. 22, 2006, which claims priority to Canadian Patent Application No. 2,524,619, filed Nov. 22, 2005.

The present invention relates to stem cells, nucleotide sequences and proteins therefrom. More specifically, the present invention relates to stem cells derived from muscle, nucleotide sequences and proteins therefrom.

BACKGROUND OF THE INVENTION

In adult skeletal muscle, satellite cells reside in a niche beneath the basal lamina but outside the associated muscle fibers and are responsible for muscle growth, maintenance and repair (Bischoff, 1994; Mauro, 1961). Satellite cells are normally mitotically quiescent, but are activated (i.e. enter the cell cycle) in response to stress induced by weight bearing or by trauma such as injury (Charge and Rudnicki, 2004). The descendants of activated satellite cells, called myogenic precursor cells, undergo multiple rounds of division prior to fusion and terminal differentiation (Dhawan and Rando, 2005). Activated satellite cells also generate progeny that restore the pool of quiescent satellite cells (Collins, 2006).

The maintenance of satellite cell numbers in aged muscle after repeated cycles of degeneration and regeneration has been interpreted to support the notion that satellite cells possess an intrinsic capacity for self-renewal (Bischoff, 1994). Asymmetric distribution of Numb protein in daughters of satellite cells in cell culture has been implicated in the asymmetric generation of distinct daughter cells for self-renewal or differentiation (Conboy and Rando, 2002). Nevertheless, the precise molecular mechanisms regulating satellite cell self-renewal and differentiation remain poorly understood.

The paired-box transcription factor Pax7 plays an important role in regulating satellite cell function. Pax7 is specifically expressed in satellite cells in adult muscle and their daughter myogenic precursor cells in vivo, and primary myoblasts in vitro (Seale et al., 2000). Extensive analysis of Pax7$^{-/-}$ mice have confirmed the progressive ablation of the satellite cell lineage in multiple muscle groups (Kuang et al., 2006; Oustanina et al., 2004; Relaix et al., 2006; Seale et al., 2000). Small numbers of Pax7-deficient cells do survive in the satellite cell position but these cells do not express the satellite cell markers CD34 and Syn4, and arrest and die upon entering mitosis (Kuang et al., 2006; Relaix et al., 2006). Muscle in Pax7-deficient mice is reduced in size, the fibers contain approximately 50% the normal number of nuclei, and fiber diameters are significantly reduced (Kuang et al., 2006). Together, these data confirm an important role for Pax7 in regulating the productive myogenic commitment of satellite cells.

Early experiments using quail-chick chimeras suggested that satellite cells were derived from the somite (Armand et al., 1983). Recent experiments support this work and indicate that the progenitors of satellite cells originate in embryonic somites as Pax3/Pax7 expressing cells (Ben-Yair and Kalcheim, 2005; Gros et al., 2005; Kassar-Duchossoy et al., 2005; Relaix et al., 2005; Schienda et al., 2006). In addition, satellite cells may also be derived from cells associated with the embryonic vasculature including the dorsal aorta (De Angelis et al., 1999), and from other adult stem cells during regeneration (Asakura et al., 2002; LaBarge and Blau, 2002; Polesskaya et al., 2003). However, whether satellite cells are stem cells, committed progenitors or de-differentiated myoblasts (Zammit et al., 2004), remains unresolved.

Several studies have suggested that the satellite cell compartment is not a homogeneous population. Radio isotope labeling of growing rat muscle revealed that satellite cells are a mixture of 80% fast cycling cells and 20% of slow cycling "reserve cells" (Schultz, 1996). Examination of the expression of satellite cell markers CD34, M-cadherin and Myf5-nLacZ in freshly prepared myofibers has suggested that a subpopulation of satellite cells may exhibit heterogeneous expression of these markers (Beauchamp et al., 2000). However, the molecular identity of any potential subpopulations has not been defined and the prospective isolation and characterization of these cells has not been achieved.

Transplantation of the cultured primary myoblasts into regenerating muscle typically results in extensive loss of the transplanted cells, terminal differentiation of the surviving cells, and virtually no contribution to the satellite cell compartment (Beauchamp et al., 1999; El Fahime et al., 2003; Fan et al., 1996; Hodgetts et al., 2000; Qu et al., 1998; Rando and Blau, 1994). By contrast, experiments involving transplant of intact fibers carrying satellite cells (Collins et al., 2005), or prospectively isolated satellite cells (Montarras et al., 2005), has suggested that a small proportion of satellite cells has the capacity to repopulate the satellite cell compartment as well as extensively contribute to regenerating muscle. Together, these results strongly support the hypothesis that sub-laminar satellite cells in vivo are a heterogeneous population containing a minor subpopulation capable of repopulating the satellite cell niche as well as giving rise to cells committed to terminal differentiation.

There is a need in the art to identify and isolate novel stem cells. Further, there is a need in the art to employ novel stem cells in therapeutic applications. There is also a need in the art to identify nucleotide sequences and genes therefrom that are involved in growth, differentiation or both growth and differentiation of stem cells, progenitor cells, myoblasts or the like.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to stem cells, nucleotide sequences and proteins therefrom. More specifically, the present invention relates to stem cells derived from muscle, nucleotide sequences and proteins therefrom.

In an embodiment, the present invention relates to an isolated pax7+/Myf5− stem cell. Satellite cells that express Pax7 but not Myf5, give rise to Myf5 expressing cells through sub-laminar asymmetric cell divisions in a basal-apical orientation. Finally, it is observed that Pax7+/Myf5− satellite cells are capable of efficiently contributing to the satellite cell reservoir following prospective isolation and transplantation into Pax7$^{-/-}$ or mdx muscle.

The present invention also provides a composition comprising the stem cell as provided above and one or more of the following:

a) a pax7+/Myf5+ progenitor cell;
b) a cell culture medium;
c) a cryopreservation medium;
d) a pharmaceutically acceptable delivery medium, or a combination thereof.

The present invention also provides a method of treating one or more diseases or disorders in a subject comprising administering Pax7+/Myf5– stem cells or a composition comprising Pax7+/Myf5– stem cells to the subject.

Also provided by the present invention is a method for isolating Pax7+/Myf5– stem cells comprising,
subjecting cells to one or more flow cytometric methods to purify or enrich for satellite stem cells that are Pax7+/Myf5–.

Typically, but not always, Pax7+/Myf5– stem cells comprise about 10% of the sublaminar satellite cells in adult skeletal muscle. Any other suitable method known in the art may also be employed to isolate Pax7+/Myf5– cells.

The present invention also provides a MEGF10 protein, fragment or variant of the amino acid sequence as shown herein.

In an alternate embodiment, there is provided a nucleotide sequence encoding a MEGF10 protein, fragment or variant of the amino acid sequence, or an antisense or siRNA sequence thereto.

The present invention also provides a method for enhancing proliferation and/or inhibiting differentiation of a stem cell, progenitor cell, or myoblast cell comprising expressing MEGF10 or an active fragment or variant thereof in the cell.

In an alternate embodiment the present invention provides an antibody against MEGF10 protein, a fragment or variant thereof.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1A shows single myofibers isolated from Myf5–nLacZ mice. 87% of Pax7+ satellite cells co-expressed Myf5 (left column), and 13% of Pax7+ cells were Myf5– (Right Column, n=3 mice). FIG. 1B shows single myofibers isolated from Myf5–Cre/ROSA-YFP reporter mice. 90% of Pax7+ cells also expressed Myf5–Cre as revealed by YFP expression (left column). Notably, 10% of Pax7+ cells were YFP– indicating that these cells have never expressed Myf5–Cre (right column, n=18 mice).

FIG. 3A is an illustration of Cre-mediated LacZ reporter gene expression in muscle from the Myf5–Cre/ROSA26R3 reporter mice. FIG. 3B shows a Pax7+/LacZ+ satellite cell, indicating Myf5–Cre was once expressed in the cell. FIG. 3C shows a Pax7+ satellite cell that was negative for LacZ, indicating Myf5–Cre was never expressed in the cell. Notice that all myonuclei are LacZ positive, indicating that Myf5 is activated during differentiation. Scale bar: 20 μm.

FIGS. 5A-C show single myofibers isolated from Myf5–nLacZ mice were stained with various markers. FIG. 5A shows a Pax7+/Myf5– satellite cell (A1, arrowhead) that is also Syn4+(A2, arrowhead). FIG. 5B shows a Pax7+/Myf5+ satellite cell (B1, arrow) expressing Syn4 (B2, arrow). FIG. 5C shows both Pax7+/Myf5– (C1, arrowhead) and Pax7+/Myf5+ (C1, arrow) satellite cells expressed M-Cad (C2). FIGS. 5D-F show single myofibers isolated from Myf5–Cre/ROSA-YFP double transgenic mice labelled with various markers. D. NCAM+/YFP– satellite cell associated with single fiber. E. NCAM+/YFP+ satellite cell. F. Pax7+/YFP– (F1, arrowhead) and Pax7+/YFP+ (F1, arrow) satellite cells both expressed CD34 (F2). Scale bar: 25 μm.

FIGS. 6A-B show clonal derived clusters of satellite cells from Myf5–Cre/ROSA-YFP reporter mice after 3 day in culture. FIG. 6A shows a cluster of satellite cells that all express YFP although some have down-regulated Pax7 expression. FIG. 6B shows a cluster of satellite cells containing both Pax7+/YFP+ (arrow) and Pax7+/YFP– (arrow head) cells. FIG. 6C shows a pair of sister satellite cells with one Pax7+/YFP– (arrow head) and one Pax7+/YFP+ (arrow) cells after 2 days in culture. FIGS. 6D-F show the induction of satellite cell proliferation in vivo on live EDL myofibers following injection of CTX into the TA muscle. FIG. 6D shows extensive proliferation of satellite cells on a regenerating EDL myofiber 4 d post CTX injection. The majority of satellite cells have undergone mitosis as indicated by the presence of two adjacent Pax7+ nuclei (double arrows) within a single satellite cell niche. FIG. 6E shows a couplet of identical sister cells that were both Pax7+/YFP+. FIG. 6F shows a couplet of sister cells with one Pax7+/YFP– cell (arrow head) and one Pax7+/YFP+ (arrow) cell. Satellite cell couplets expressed the metaphase mitosis marker phosphorylated histone-H3 (FIG. 6G), and the proliferation marker Ki67 (FIG. 6H). In H, β-Gal labelling denotes Myf5–nLacZ expression. Scale bars: 20 μm in A, B, D; 10 μm in C, E, F, G, H.

FIG. 8A shows that planar cell divisions occur parallel to the basal lamina, whereas FIG. 8B shows that apical-basal cell divisions occur at a 90° angle to the basal lamina. Satellite cells (red and green cells) are located beneath the basal lamina (green) and adjacent to the myofiber (brown). Overall, 92% (n=89) of planar divisions were symmetrical (Sym) in terms of Pax7 and Myf5 expression (A). By contrast, 82% (n=38) of apical-basal divisions were asymmetrical (Asym) as judged by differential Pax7 and Myf5 expression in sister cells (B). FIG. 8C shows that planar divisions uniformly occurred such that sister cells (double arrows) remained within the satellite cell niche between laminin (Lam) on the basal surface, and M-cadherin (M-Cad) on the apical surface against the muscle fiber. FIG. 8D shows that apical-basal cell divisions were also uniformly beneath the basal lamina where both sister cells (double arrows) expressed Pax7. FIGS. 8E-F show regenerating myofibers isolated from EDL muscle from Myf5–Cre/ROSA-YFP reporter mice exhibiting both planar (double arrows) and apical-basal (arrow and arrowhead in F) oriented sister satellite cells. Planar cell divisions were typically symmetric as indicated by the identical expression of Pax7 and YFP in sister cells. However, apical-basal cell divisions were typically asymmetric generating a basal Pax7+/YFPcell (arrow) and an apical Pax7+/YFP+ cell (arrowhead). FIG. 8G-H show regenerating myofibers from EDL muscle from Myf5–nLacZ mice similarly exhibited symmetrical planar (double arrows in G) and asymmetric apical-basal (arrow and arrowhead in H) oriented sister satellite cells. Centrally located myonuclei confirm the regenerating status of the myofibers. Scale bar: 12.5 µm.

FIG. 9A shows that satellite cells traverse the basal lamina in cell culture resulting in an inverted relationship to the myofiber. 24 hr after isolation of individual Myf5–nLacZ myofibers, satellite cells were located on the outside surface of the basal lamina, but still maintained M-Cad expression on the membrane opposing the basal lamina. FIG. 9B shows that apical-basal oriented sister cells with differential expression of Pax7 and Myf5. The basal cell is Pax7High/Myf5Low whereas the apical cell is Pax7Low/Myf5High. FIG. 9C shows that planar oriented sister cells displayed identical levels of Pax7 and Myf5 expression. Scale bar: 20 µm.

FIG. 10A shows the expression of α7integrin in satellite cells associated with single myofiber isolated from Myf5–Cre/ROSA-YFP double transgenic mouse. Both YFP+ (arrowhead) and YFP– (arrow) satellite cells expressed α7integrin. The bright α7integrin signal to the right of A1 and A4 is from the myotendinous junction. Scale bar: 20 µm. FIG. 10B shows FACS isolation of α7integrin+ and α7integrin-cells derived from limb muscles. Cells were first negatively selected with antibodies reactive to CD31, CD45, and Ter119 to remove endothelial cells, haematopoietic cells and erythrocytes, respectively (left column), and positively selected for α7integrin (middle column). FIG. 10C shows gene expression profile of α7integrin+ and α7integrin– cells. Pax7, Myf5 and Cre transcripts are only detectable in the α7integrin+/CD31–/CD45–/Ter119– cells. SA-YFP (Neo Cassette excised ROSA-YFP transcript) was present in both fractions.

FIG. 11A is a FACS analysis of limb muscle derived cells from Myf5–Cre/ROSA-YFP reporter mice. Isolation of Pax7+/Myf5+ satellite cells was performed by sorting for cells that expressed YFP (middle column). To isolate Pax7+/Myf5– satellite cells, mononuclear cells were first negatively selected with antibodies reactive to Sca1, CD31, CD45, and Ter119 to remove fibroblasts, endothelial cells, haematopoietic cells and erythrocytes respectively (left column). Second, cells were positively sorted for α7-integrin expression (right column). FIG. 11B is a RT-PCR analysis of YFP+ versus YFP–/α7integrin+/Sca1–/CD31–/CD45–/Ter119– cells (denoted YFP–α7Int+) confirmed the efficacy of the sort strategy. Expression of Pax7 was detected in both fractions, but with reduced levels in the YFP–α7Int+ fraction. Expression of Myf5, Cre and SA-YFP (Neo Cassette excised ROSA-YFP transcript) was only detectable in YFP+ fraction. Interestingly, Notch-3 was predominantly expressed in YFP– cells whereas Delta-1 was predominantly expressed in YFP+ α7Int+ cells. FIG. 11C shows the expression of Pax7 in FACS isolated YFP+ (upper panels) and YFP–/α7Int+ (lower panels) cells. Overall, 89±6% of the cells from YFP+ fraction expressed Pax7 (n=4), whereas 20±5% of cells from the fraction expressed Pax7 (n=4). Scale bar: 25 µm.

FIG. 12A: regenerating TA muscles were grafted with 3,000 freshly isolated YFP+ satellite cells and examined 3 weeks later. FIG. 12A1—expression of dystrophin (white staining). FIG. 12A2—donor-derived YFP+ satellite cells (arrowheads) associated with donor-derived Dystrophin+/YFP+ myofibers. FIG. 12A3—Occasional donor-derived mononuclear YFP+ cells (arrowheads) were also observed in the interstitial environment. FIG. 12B: regenerating TA muscles were grafted with 3,000 freshly isolated YFP-á7int+ cells and examined 3 weeks later. FIG. 12B1—expression of dystrophin (white staining). FIG. 12B2 and FIG. 12B3—donor YFP–α7int+ satellite cells gave rise to YFP+ (arrowheads) and YFP– (arrow) satellite cells associated with Dystrophin+ myofibers. FIG. 12C1 and FIG. 12C2—ten and twenty thousand, respectively, freshly isolated YFP+ satellite cells were grafted into the TA muscles of Pax7–/– mice and examined 3 weeks later. Transplanted YFP+ cells preferentially differentiated to form YFP+ myotubes. FIG. 12C2—rare donor-derived Pax7+/YFP+ satellite cells (arrowhead) were observed and these were always associated with YFP+ myofibers. FIG. 12D1 and FIG. 12D2—TA muscle of Pax7–/– mouse grafted with 20,000 freshly isolated YFP–/á7int+ satellite cells and examined 3 weeks later. FIG. 12D1—Transplanted YFP–/α7int+ satellite cells gave rise to numerous Pax7+/YFP– (arrows) and Pax7+/YFP+ (arrowhead) cells closely associated with host myofibers. FIG. 12D2—-sub-laminar localization of the donor derived Pax7+ cells (arrow) was confirmed by anti-laminin labelling. Scale bars: 50 µm in A1 and B1; 25 µm in C1, D1; and 12.5 µm for the rest of the panels.

DESCRIPTION OF PREFERRED EMBODIMENT

Figure 1:
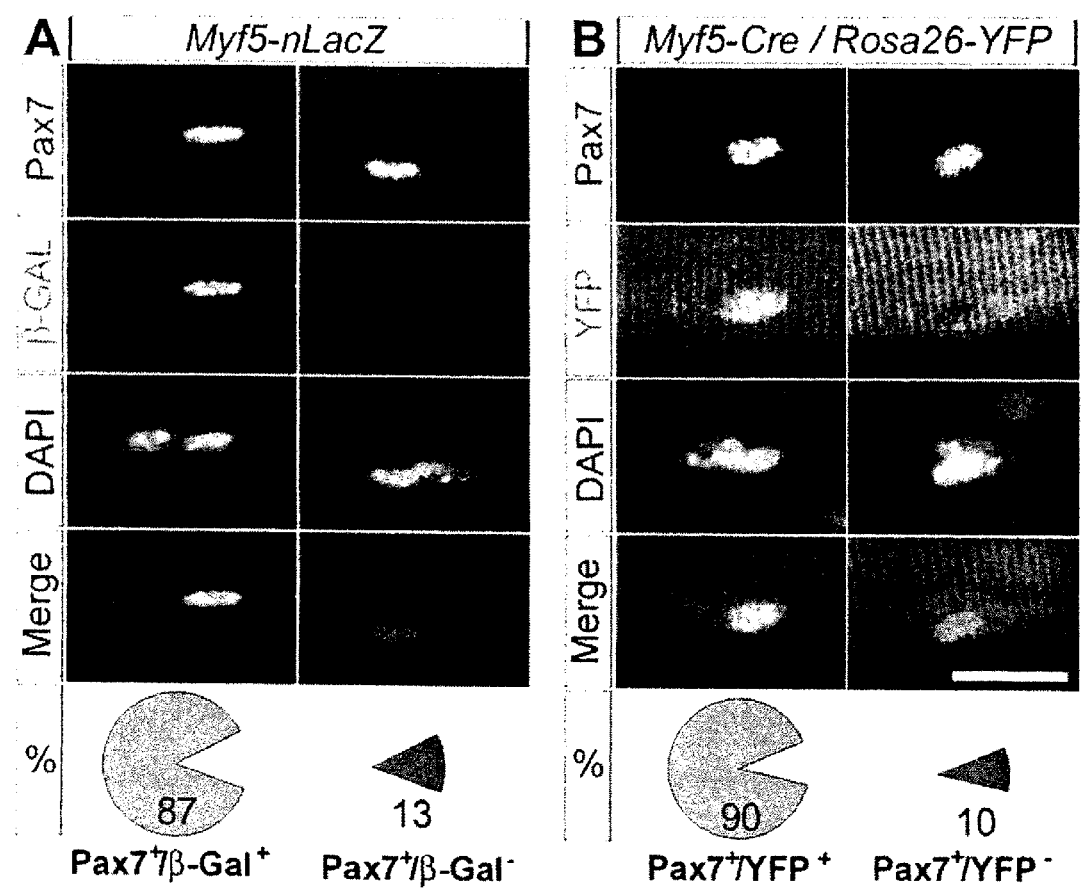
FIG. 1 shows that satellite cells are a heterogeneous population based on Myf5 expression.

The present invention relates to stem cells, nucleotide sequences and proteins therefrom. More specifically, the present invention relates to stem cells derived from muscle, nucleotide sequences and proteins therefrom.

The following description is of a preferred embodiment by way of example only and without limitation to the combination of features necessary for carrying the invention into effect. All disclosures made throughout the description that pertain to one or more mechanisms to arrive at or promote a desired effect are not meant to be bound by theory or limiting in any manner.

A mechanism underlying stem cell self-renewal and differentiation is asymmetrical division, resulting in one stem cell and one differentiating cell. Although certain stem-cell features have been established in muscle satellite cells (MSCs), it had previously remained unknown whether all MSCs act as stem cells, and how MSCs accomplish self-renewal and differentiation during growth and regeneration remained an open question.

Based on research that was conducted and the results of several experiments, it was observed that the MSC population is heterogenous based on the expression of at least two transcriptional factors: Pax7 and Myf5. Whereas the majority of MSCs express both Pax7 and Myf5 (Pax7+/Myf5+), a small population (about 10%) of MSCs express only Pax7 (Pax7+/Myf5−). Genetic analysis in mouse using Cre-LoxP system demonstrates that the Pax7+/Myf5− population have never expressed Myf5 in the past. Therefore the Pax7+/Myf5− MSCs represent a novel stem cell population and the majority Pax7+/Myf5+ MSCs represent the myogenic progenitor cell population. During muscle regeneration, both Myf5+ and Myf5− MSCs proliferate, but the Pax7+/Myf5− stem cells can undergo asymmetrical division to self renew and give rise to Pax7+/Myf5+ progenitor cells. The fate of daughter cells in vivo is determined by their relative position within the MSC niche and by the orientation of cell division. A planar division is symmetrical, generating two daughter cells wherein both remain to be Pax7+/Myf5−. By contrast, an apico-basal division is asymmetrical, with the basal cell remaining as Myf5− and the apical cell starting to express Myf5. Without wishing to be limiting in any manner, it is proposed that the MSC niche, which contains laminin and β1-integrin on the basal side and M-cadherin on the apical side, controls the self-renewal and differentiation of the Pax7+/Myf5− stem cells, with the basal laminin playing a role in maintaining the stemness of these cells.

According to an embodiment of the present invention, there is provided an isolated Pax7+/Myf5− muscle stem cell or a composition comprising Pax7+/Myf5-muscle stem cells. The muscle stem cell or muscle satellite stem cell may be derived from muscle, preferably skeletal muscle of any mammalian subject, for example, but not limited to human, rat, mouse, rabbit, pig, goat, chimpanzee, guinea pig, horse or the like. In a preferred embodiment, the Pax7+/Myf5− stem cell is a human muscle stem cell.

In a further embodiment, the muscle stem cells of the present invention may comprise one or more additional markers. The term "marker" refers to a characteristic or trait which permits the identification, selection, screening, isolation or any combination thereof of the muscle stem cells of the present invention. Without wishing to be limiting, a marker may comprise a protein or portion thereof which is located on the cell surface of muscle stem cell, but not other cells. Alternatively, a marker may comprise an oligosaccharide, polysaccharide, lipid, protein such as but not limited to a membrane receptor or the like, or any combination thereof that differentiates the muscle stem cells of the present invention from other cells. Further a marker may comprise the expression (or non-expression) of a nucleotide sequence or gene of interest or may comprise the expression pattern of one or more genes of interest. For example, but not wishing to be limiting in any manner, the present invention provides muscle stem cells that are Pax 7+/Myf5− cells. The muscle stem cells may further comprise CD34, M-CAD, Syn 4 (Syndecan4), N-CAM, α7-integrin, β1-integrin or a combination thereof. In an embodiment of the present invention, the muscle stem cells comprise CD34, M-CAD, Syn 4, N-CAM, α7-integrin and β1-integrin. Further, it is contemplated that the muscle stem cells of the present invention may lack one or more markers which are typically associated with other types of cells that are not muscle stem cells or muscle satellite cells. For example, such markers may include, but are not limited to Sca1, CD31, CD45, Ter119, MEGF-10 or a combination thereof. Accordingly, but not wishing to be limiting in any manner, the present invention contemplates muscle stem cells that are Pax7+/Myf5−/CD34+/Sca1−/MEGF10− cells. In an alternate embodiments, the present invention contemplates Pax7+/Myf5+/CD34+/Sca1−/MEGF10−, Pax7+/Myf5−/CD34+/Sca1−/MEGF10+, Pax7+/Myf5+/CD34+/Sca1−/MEGF10+ satellite stem cells. Also, as will be evident based on the disclosure herein, a Pax7+/Myf5−, CD34+/Sca1−/MEGF10− satellite stem cells may become Pax7+/Myf5−, CD34+/Sca1−/MEGF10+ by transforming the cell with a nucleotide construct expressing MEGF10. A person of skill in the art will recognize that other combinations of markers or lack thereof may characterize and/or define the muscle stem cells of the present invention as provided herein.

In an embodiment of the present invention, the markers as defined above may be employed in methods for the identification, selection, screening, isolation or any combination thereof of the muscle stem cells of the present invention. In an embodiment, which is not meant to be limiting in any manner, the markers may be employed in flow cytometric analysis or FACS to enrich or purify specific populations of cells, including, but not limited to Pax7+/Myf5− muscle stem cells, Pax7+/Myf5+ progenitor cells, or both. For example, but not to be considered limiting, a combination of alpha7-integrin and beta1-integrin expression may be employed in methods to identify the entire muscle satellite stem cell pool.

As described above, the present invention contemplates compositions comprising Pax7+/Myf5− muscle stem cells. In a further embodiment, the composition may comprise Pax7+/Myf5− stem cells and Pax7+/Myf5+ progenitor cells. Preferably the ratio of Pax7+/Myf5− stem cells to Pax7+/Myf5+ progenitor cells is greater than about 1:20, preferably 1:10, more preferably about 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 50:1, 100:1, 1000:1, 10000:1, 100000:1 or higher. However, the present invention contemplates compositions wherein the ratio of Pax7+/Myf5− stem cells to Pax7+/Myf5+ progenitor cells is defined by a range of any two of the values listed above, or any amount therebetween.

It is also contemplated that Pax7+/Myf5− stem cells may be transformed with one or more heterologous nucleic acids or nucleic acid constructs. The present invention contemplates transforming Pax7+/Myf5− stem cells or both Pax7+/Myf5− cells and Pax7+/Myf5+ cells with any nucleic acid or nucleic acid construct. For example, but not wishing to be limiting, the cells as described above may be transformed with a nucleotide sequence that is capable of expressing a normal or wild-type protein that is defective or mutated in the subject from which the cells were obtained. In this way the transformed cells may be used in a gene therapy approach to replace muscle cells containing defective genes or the like. It is also contemplated that the muscle stem cells or compositions of muscle stem cells as described herein may be isolated from a first subject, optionally transformed with one or more nucleotide sequences as described above and implanted into a second subject.

Compositions comprising Pax7+/Myf5− stem cells may comprise a medium, for example, but not limited to a cell culture or growth medium, cryopreservation medium, a pharmaceutically acceptable delivery medium or any combination thereof. A variety of liquid or solid medias (or combination thereof) may be used for the isolation, manipulation, cell culture, cryopreservation, administration or transplantation of cells, as would be understood by a person of skill in the art.

In an embodiment of the present invention, Pax7+/Myf5− stem cells may be cultured in a suitable medium. In a further non-limiting embodiment, Pax7+/Myf5− stem cells may be cultured to proliferate, thereby producing additional Pax7+/Myf5− stem cells. In still an alternate embodiment, the Pax7+/Myf5− stem cells may be cultured to produce progenitor cells, for example, but not limited to Pax7+/Myf5+ progenitor cells.

Pax7+/Myf5− stem cells or compositions comprising Pax7+/Myf5− stem cells as described herein may be employed for transplantation in a subject for treatment of one or more diseases or disorders, for example, but not limited to one or more muscle diseases or disorders. Examples of muscular diseases include, but are not limited to muscular dystrophies.

Muscular dystrophies are genetic diseases characterized by progressive weakness and degeneration of the skeletal or voluntary muscles which control movement. The muscles of the heart and some other involuntary muscles are also affected in some forms of muscular dystrophy. In many cases, the histological picture shows variation in fiber size, muscle cell necrosis and regeneration, and often proliferation of connective and adipose tissue. Examples of muscular dystrophies include, but are not limited to Duchenne muscular dystrophy (DMD), Becker muscular dystrophy (BMD), myotonic dystrophy (also known as Steinert's disease), limb-girdle muscular dystrophies, facioscapulohumeral muscular dystrophies (FSH), congenital muscular dystrophies, oculopharyngeal muscular dystrophy (OPMD), distal muscular dystrophies and Emery-Dreifuss muscular dystrophy. See, e.g., Hoffman et al., N. Engl. J. Med., 318.1363-1368 (1988); Bonnemann, C. G. et al., Curr. Opin. Ped., 8: 569-582 (1996); Worton, R., Science, 270: 755-756 (1995); Funakoshi, M. et al., Neuromuscul. Disord., 9 (2): 108-114 (1999); Lim, L. E. and Campbell, K. P., Cure. Opin. Neurol., 11 (5): 443-452 (1998); Voit, T., Brain Dev., 20 (2): 65-74 (1998); Brown, R. H., Annu. Rev. Med., 48: 457-466 (1997); Fisher, J. and Upadhyaya, M., Neuromuscul. Disord., 7 (1): 55-62 (1997).

While the preceding paragraph provides one or more muscular diseases or disorders that may be treated by the Pax7+/Myf5− stem cells and compositions comprising Pax7+/Myf5− stem cells, due to their pluripotential nature, the stem cells may be used in the treatment of a variety of diseases and disorders including non-muscle diseases and disorders. Further, in addition to using the stem cells in transplants, Pax7+/Myf5− stem cells, or compositions comprising Pax7+/Myf5− stem cells may be used as a research tool and/or as part of a diagnostic assay or kit. Without wishing to be limiting a kit may comprise Pax7+/Myf5− muscle stem cells, Pax7+/myf5+ progenitor cells, cell culture or growth medium, cell cryopreservation medium, one or more pharmaceutically acceptable delivery media, one or more nucleotide sequences or genetic constructs, one or more devices for implantation or delivery of cells to a subject in need thereof, instructions for using, delivering, implanting, culturing, cryopreserving or any combination thereof the cells as described herein.

In embodiments where Pax7+/Myf5− stem cells from a donor subject are transplanted into a recipient subject in need thereof, preferably, the donor and recipient are matched for immunocompatibility. For example, but not wishing to be limiting, it is preferable that the donor and the recipient are matched for compatibility to the major histocompatibility complex (MHC) (human leukocyte antigen (HLA))-class I (e.g., loci A, B, C) and -class II (e.g., loci DR, DQ, DRW) antigens. Immunocompatibility between donor and recipient may be determined according to methods generally known in the art (see, e.g., Charron, D. J., Curr. Opin. Hematol., 3: 416-422 (1996); Goldman, J., Curr. Opin. Hematol., 5: 417-418 (1998); and Boisjoly, H. M. et al., Opthalmology, 93: 1290-1297 (1986)).

Pax7+/Myf5− stem cells or a composition comprising Pax7+/Myf5− stem cells may administered to a subject by any suitable method and/or route known in the art. In an embodiment, the stem cells or compositions comprising stem cells are administered into tissue of a subject. These tissues may include but are not limited to muscle including but not limited to smooth, striated, skeletal, cardiac or a combination thereof, skin, lung, liver, spleen, bone marrow, thymus, heart, lymph, bone, cartilage, pancreas, kidney, gall bladder, stomach, intestine, testis, ovary, uterus, rectum, nervous system including but not limited to brain or spinal chord, eye, gland, connective tissue, blood, tumor, and the like. The administration may be made by intradermal, subdermal, intravenous, intramuscular, intranasal, intracerebral, intratracheal, intraarterial, intraperitoneal, intravesical, intrapleural, intracoronary or intratumoral injection, with a syringe or other suitable device. In a preferred embodiment, Pax7+/Myf5− stem cells or a composition comprising Pax7+/Myf5− stem cells is injected into muscle tissue, preferably in an area proximal to diseased, injured or damaged tissue. However, injection into the circulation or at a distal site is also contemplated by the present invention.

Based on the disclosure provided above and the additional information provided herein and throughout, the present invention provides a method of treating a disease, disorder, injury or the like in a subject comprising,
  administering Pax7+/Myf5− stem cells or a composition comprising Pax7+/Myf5− stem cells to a subject in need thereof.

In an embodiment wherein the disease is a muscle disease or neuromuscular disease, preferably the cells are injected intramuscularly.

The present invention also contemplates a method of purifying and/or isolating Pax7+/Myf5− stem cells from other cells including, but not limited to Pax7+/Myf5+ muscle progenitor cells. Any method known in the art may be employed for this purpose having regard to the characteristics of the muscle stem cells as described herein. In a preferred embodiment, but not to be considered limiting in any manner, the cells may be isolated and/or purified based on cell surface markers using fluoroescence assisted cell sorting (FACS). For example, satellite stem cells are CD34+/Sca1−/MEGF10−, whereas satellite myogenic cells are CD34+/Sca1−/MEGF10+. It is also contemplated that α7-integrin and Syndecan4 may be used as cell surface markers to sort satellite stem cells and satellite myogenic cells from other cells. Further, in terms of other markers examined, PCR array amalysis indicated that Cdh2 (cadherin 2 or neuronal cadherin) was expressed in YFP− cells, but very low in YFP+ cell. This provides yet another marker that may be used to assist in sorting, purifying or isolating the cells of the present invention.

Also provided by the present invention is a stem cell niche comprising a muscle fiber or portion thereof comprising one or more sublaminar Pax7+/Myf5− cells, said cells optionally in apico/basal orientation with one or more Pax7+/Myf5+ cells, wherein the basal cells are Pax7+/Myf5− cells and the apical cells are Pax7+/Myf5+ cells.

A variety of methods are known in the art to determine if a cell or a group of cells is expressing Pax7 and/or Myf5 (or one or more other genes or nucleotide sequences). For example, but not wishing to be considered limiting, the expression of Pax7 and/or Myf5 genes may be monitored by PCR, for example, but not limited to RT-PCR or the like. Similarly, Pax7 and/or Myf5 gene products may be identified by a variety of immunocytochemical methods as is known in the art.

Further embodiments of the present invention are illustrated in the figures and examples as provided herein.

MEGF10 Nucleotide Sequence and Proteins Therefrom

MEGF10 is a novel mouse nucleotide sequence that encodes a multiple EGF-repeat containing transmembrane protein. Immunocytochemistry and immunohistochemistry revealed that MEGF10 is expressed in adult skeletal muscle specifically in a subset of quiescent satellite cells. MEGF10 is also expressed at low levels in proliferating myoblasts and is downregulated as these cells differentiate to form multinucleated myotubes. Retroviral infection and forced over-expression of MEGF10 in C2C12 myoblasts leads to enhanced proliferation of these cells. This effect appears to be specific to myogenic cells and does not occur when MEGF10 is overexpressed in 10T1/2 fibroblasts. As well as enhancing proliferation, overexpression of MEGF10 in myogenic cells also inhibits differentiation. Interestingly, cells overexpressing MEGF10 appear to become quiescent following serum withdrawal rather than undergoing terminal differentiation. Furthermore, these cells can be stimulated to re-enter the cell cycle following extended culture under low serum conditions. Thus, these cells appear to function in a manner similar to "reserve cells". At a molecular level, MEGF10 is capable of altering the expression of several key myogenic proteins including Myf5, MyoD, and Pax7. Forced expression of MEGF10 results in the upregulation of Myf5 and downregulation of Pax7 at the level of RNA transcripts. It also downregulates MyoD protein without affecting the levels of MyoD RNA. When the cytoplasmic domain of MEGF10 is removed (the carboxy terminal 290 amino acids) MEGF10 overexpression no longer alters the levels of these myogenic factors. Furthermore, the proliferation and differentiation effects are abolished. The potential mechanism by which MEGF10 signaling effects expression of myogenic proteins and alters proliferation and differentiation is the MAP kinase signaling pathway. Over expression of MEGF10 results in elevated levels of phosphorylated MEK1/2 while the total level of MEK1/2 in these cells is actually decreased. Interestingly, activated MEK1/2 does not result in increased levels of activated ERK1/2 in cells over expressing MEGF10. Taken together, this suggests that activated MEK1/2 is being translocated to the nucleus where it alters MyoD stability and affects proliferation and differentiation. Immunostaining revealed that daughter Pax7+/Myf5+ cells specifically express MEGF10 whereas the parent Pax7+/Myf5– stem cell does not. Without wishing to be bound by theory or limiting in any manner, the data indicates that MEGF10 has a role in suppressing the progression of daughter cells through the myogenic developmental program to keep the cell in a quiescent state in the sublaminar satellite cell position.

According to an embodiment of the present invention, there is provided a MEGF protein comprising or consisting of the following amino acid sequence or a fragment thereof:

(SEQ ID NO: 1)
MAISSSSCLGLICSLLCHWVGTASSLNLEDPNVCSHWESYSVTVQESYPH

PFDQIYYTSCTDILNWFKCTRHRISYRTAYRHGEKTMYRRKSQCCPGFYE

SRDMCVPHCADKCVHGRCIAPNTCQCEPGWGGTNCSSACDGDHWGPHCSS

RCQCKNRALCNPITGACHCAAGYRGWRCEDRCEQGTYGNDCHQRCQRQNG

ATCDHITGECRCSPGYTGAFCEDLCPPGKHGPHCEQRCPCQNGGVCHHVT

GECSCPSGWMGTVCGQPCPEGRFGKNCSQECQCHNGGTCDAATGQCHCSP

GYTGERCQDECPVGSYGVRCAEACRCVNGGKCYHVSGTCLCEAGFSGELC

EARICPEGLYGIKCDKRCPCHLDNTHSCHPMSGECGCKPGWSGLYCNETC

SPGFYGEACQQICSCQNGADCDSVTGRCACAPGFKGTDCSTPCPLGRYGI

NCSSRCGCKNDAVCSPVDGSCICKAGWHGVDCSIRCPSGTWGFGCNLTCQ

CLNGGACNTLDGTCTCAPGWRGAKCEFPCQDGTYGLNCAERCDCSHADGC

HPTTGHCRCLPGWSGVHCDSVCAEGRWGPNCSLPCYCKNXASCSPDXGIC

ECAPGFRGTTCQRICSPGFYGHRCSQTCPQCVHSSGPCHHITGLCDCLPF

FTGALCNEVCPSGRFGKNCAGVCTCTNNGTCNPIDRSCQCYPGWIGSDCS

QPCPPAHWGPNCIHTCNCHNGAFCSAYDGECKCTPGWTGLYCTQRCPLGF

YGKDCALICQCQNGADCDHISGQCTCRTGFMGRHCEQKCPAGTYGYGCRQ

ICDCLNNSTCDHITGTCYCSPGWKGARCDQAGVIIVGNLNSLSRTSTALP

ADSYQIGAIAGIVVLVLVVLFLLALFIIYRHKQKRKESSMPAVTYTPAMR

VINADYTIAETLPHSNGGNANSHYFTNPSYHTLSQCATSPHVNNRDRMTI

AKSKNNQLFVNLKNVNPGKRGTLVDCTGTLPADWKQGGYLNELGAFGLDR

SYMGKSLKDLGKNSEYNSSTCSLSSSENPYATIKDPPALLPKSSECGYVE

MKSPARRDPSPYAEINNSTPANRNVYEVEPTVSVVQGVFSNSGHVTQDPY

DLPKNSHIPCHYDLLPVRDSSSSPKREDGGGSNSTSSNSTSSSSSSS

Fragments of MEGF10 include, but are not limited to amino acid sequences wherein one or more amino acids from MEGF10 are deleted. For example, but not to be considered limiting, a fragment of MEGF10 exists when the cytoplasmic domain (the carboxy terminal 290 amino acids) of MEGF10 is removed. However, the present invention also contemplates fragments wherein one or more amino acids from the amino terminal, carboxy terminal or both are removed. Further, one or more amino acids internal to the polypeptide may be deleted. Preferably, the resulting fragment is not identical to a continuous amino acid sequence found in human MEGF10.

It is also contemplated that the MEGF10 protein comprises one or more amino acid substitutions, additions, insertions, or a combination thereof in the MEGF10 sequence shown herein. Such proteins may be termed MEGF10 variants. Preferably, the amino acid sequence exhibits greater than about 90% homology, more preferably greater than about 91%, 92%, 93%, 94%, 95%, 96%, 97%, 98%, 99% or about 100% homology to the MEGF10 sequence. The degree of homology may also be represented by a range defined by any two of the values listed above or any value therein between.

It is further contemplated that the amino acid sequence comprises greater than about 70%, more preferably about 80%, 85%, 90%, 91%, 92%, 93%, 94%, 95%, 96%, 97%, 98%, 99% or about 100% identity with the amino acid sequence of MEGF10. Further, the degree of identity may be represented by a range defined by any two of the values listed or any value therein between. Methods for determining % identity or % homology are known in the art and any suitable method may be employed for this purpose.

The present invention also provides a nucleic acid sequence encoding a MEGF10 protein, for example, but not limited to, MEGF10, fragments, or variants thereof. Also contemplated by the present invention are one or more nucleic acid sequences that may be used as probes to identify MEGF10 encoding genes in a cell, one or more nucleic acid primers, for example, to identify and quantitate genomic MEGF10 encoding sequences or mRNA produced therefrom, one or more antisense or siRNA nucleic acid to downregulate MEGF10 protein, or any combination thereof.

In an embodiment of the present invention, the nucleotide sequence comprises or consists of:

(SEQ ID NO: 2)
```
atggcgatttcttcaagttcgtgcctgggcctcatctgctcactgctctg
tcactgggtggggacagcatcctccctgaacctggaagaccccaacgtat
gcagccactgggaaagctactcggtgactgtgcaggagtcgtatccacat
cccttcgatcagatctactacaagctgcaccgacatcctgaactggtt
taaatgcacacggcacagaatcagctaccggacagcctaccgcacgggg
agaaaccatgtatagacgcaaatcccagtgttgcccaggattttatgaa
agccgagacatgtgtgtccctcactgtgctgataaatgtgtccatggtcg
ctgcattgctccaaacacctgtcagtgtgagcctggctggggtgggacca
actgtagcagtgcttgtgatggtgatcactgggggcctcactgcagcagc
cgatgccagtgcaaaaacagagctttgtgtaaccccatcaccggtgcttg
ccactgcgctgcgggctaccggggatggcgctgcgaggaccgttgtgaac
agggcacgtacggtaacgactgtcaccaaagatgccagcgtcagaatggg
gcgacctgtgaccacatcactggggaatgccgttgttcacctgggtacac
tggagccttctgtgaggatctttgtcctcctggcaaacatggtccacatt
gtgagcagaggtgtccctgccaaaatgggggcgtgtgccaccatgtcact
ggagagtgctcttgccttctggttggatgggcacagtgtgtggtcagcc
ctgccctgagggtcgctttggaaagaactgttcccaagaatgccagtgtc
acaatggaggaacgtgtgatgctgccacaggccagtgtcactgcagccca
ggatacacagggaacggtgtcaggacgaatgtcctgttgggagctatgg
agttcgctgtgctgaggcctgcaggtgtgtcaacggagggaagtgttacc
acgtgagtggcacatgcctgtgcgaagcaggcttttcgggtgaactttgc
gaggcgcgcctgtgtcccgaggggctttacggcatcaaatgtgacaagcg
gtgccctgccacctggacaacactcacagctgtcatcccatgtctggag
agtgtggctgcaagccgggttggtcgggactgtactgtaatgaaacatgc
tcccctggattctacggggaggcttgccaacagatctgcagctgccagaa
cggggcggactgcgacagtgtgactggaaggtgtgcctgcgctccaggat
tcaaagggactgactgctctactccgtgtcctctgggacgctacgggata
aattgttcttctcgctgtggctgtaaaaatgatgctgtctgttctcctgt
ggatggatcatgtatctgtaaggcaggctggcacggggtggactgttcca
tccgctgcccagtggcacatggggctttggctgtaacctaacgtgtcag
tgcctcaatggcggtgcctgcaacacgctggatgggacctgcacctgtgc
gcccggatggcgaggcgcgaagtgtgaatttccctgccaggatggcactt
atgggctgaactgtgccgagcgctgtgactgcagccatgcagatggctgt
caccccactacaggccattgccgctgcctccctggatggtcaggtgtgca
ctgtgacagtgtgtgcgctgagggacgctggggtcctaactgctcgctgc
cctgctactgtaaaaatrgrgcttcgtgttctccggatgawggcatctgt
gagtgtgcacccggattccgaggcaccacttgccagagaatctgctcccc
```

-continued
```
cggttttatggacatcgctgtagccagacctgcccgcagtgtgtgcaca
gcagtgggccctgccaccacatcacgggcctgtgtgactgcttacctttc
ttcaccggtgccctgtgcaatgaagtgtgtcccagtggcagatgggaaaa
actgtgcaggcgtttgtacttgcaccaacaatggcacctgtaaccccatc
gacagatcctgccagtgttacccaggctggattggcagtgactgctccca
gccctgtccacctgcgcactgggcccgaactgcatccacacctgcaactg
ccacaacggagccttttgcagcgcctatgayggggaatgcaaatgcactc
ctggctggacggggctctactgcactcagagatgccctctgggcttctat
ggtaaggactgtgcactgatatgccatgtcaaaacggagctgactgcgac
catatctcggggcagtgtacctgccgcacgggattcatgggacggcactg
tgaacagaagtgccctgcgggaacatacggctatggctgtcgccagatct
ggactgtctgaaccaactccacctgtgaccacatcactggcacgttactg
tagcccaggatggaaaggggcacgatgtgaccagctggggttatcatcgt
gggcaatctgaacagcttaagccggaccagcaccgcccttcctgccgatt
cctatcagatcggggccatcgcgggcatcgtggtcctcgttcttgttgtg
ctcttcctgctggcgctgttcatcatctacagacacaagcagaagaggaa
ggaatcaagcatgccggccgtgacctacaccccgccatgagggtcatca
atgcagactataccatcgcagaaccctgcctcacagcaatggtggaaat
gccaacagccactactttaccaatcccagttatcacacacttagccagtg
tgccacatcccctcatgtgaacaatagggacaggatgaccattgcaaagt
caaaaaacaatcagctgtttgtgaatcttaaaaatgtgaatccaggaag
agagggacattggtggactgcactgggacattgccagctgactggaagca
aggaggctacctcaatgagcttggtgctttcgggctggacagaagctaca
tgggaaagtccttaaaagatctggggaagaactctgaatataattcaagc
acttgctccttaagcagctctgaaaacccatatgccaccattaaagaccc
gcctgcactcctgcctaaaagctccgagtgcggctacgtggagatgaagt
cgccggcgcggagagactccccatatgcagagatcaacaactcaactcca
gccaacaggaatgtctatgaagtcgaacctacagtgagcgttgtgcaagg
agtattcagcaacagcggtcacgtcacccaagacccatgaccttccaa
agaacagtcacatcccttgccattatgacctgctgccagtaagggacagt
tcatcctcccaaagagagaggatggtggtggcagcaacagcaccagcag
caacagcaccagcagcagcagcagcagcagtga.
```

The nucleotide sequences provided by the present invention may be part of a larger nucleotide sequence or nucleotide construct optionally comprising one or more regulatory sequences, for example promoters, terminators and the like. By the terms "regulatory sequence", "regulatory region", "regulatory element" it is meant a portion of nucleic acid typically, but not always, upstream of the protein coding region of a nucleotide sequence, which may be comprised of either DNA or RNA, or both DNA and RNA. When a regulatory region is active, and in operative association with a nucleotide sequence of interest, this may result in expression of the nucleotide sequence of interest. A regulatory element may be capable of mediating organ specificity, or controlling developmental or temporal nucleotide sequence activation. A "regulatory region" includes promoter elements, core promoter elements exhibiting a basal promoter activity, elements that are inducible in response to a stimulus, elements that mediate promoter activity such as negative regulatory elements or transcriptional enhancers. "Regulatory region", as used herein, also includes elements that are active following transcription, for example, regulatory elements that modulate nucleotide sequence expression such as translational and transcriptional enhancers, translational and transcriptional repressors, upstream activating sequences, and mRNA instability determinants. Several of these latter elements may be located proximal to the coding region.

In the context of this disclosure, the term "regulatory sequence" "regulatory element" or "regulatory region" typically refers to a sequence of DNA, usually, but not always, upstream (5') to the coding sequence of a structural gene or nucleotide sequence of interest, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a nucleotide sequence under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within a subject as well.

In an embodiment of the present invention, which is not meant to be limiting in any manner, there is provided a vector comprising an expressible sequence encoding MEGF10 protein, a variant or fragment thereof. In an alternate embodiment, there is a vector comprising an expressible antisense sequence or siRNA that is capable of downregulating MEGF protein.

Nucleic acids comprising a sequence that encodes MEGF 0, a variant or fragment thereof can be cloned into a vector using standard techniques that are well known in the art. The vector may comprise, but is not limited to chromosomal, non-chromosomal or synthetic DNA sequences, for example, but not limited to derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies.

Viral based systems provide the advantage of being able to introduce relatively high levels of a heterologous nucleic acid into a variety of cells. Suitable viral vectors for preparation of the MEGF10-encoding vectors are well known in the art, for example, but not limited to Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

The present invention also contemplates retroviral vectors comprising MEGF10 nucleic acids. Retroviral vectors are well known in the art. Without wishing to be limiting, many retroviral vectors comprise an expression cassette encoding an heterologous gene residing between two retroviral LTRs. Retroviral vectors typically contain appropriate packaging signals that enable the retroviral vector, or RNA transcribed using the retroviral vector as a template, to be packaged into a virion in an appropriate packaging cell line (see, for example, U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the MMTV vectors (U.S. Pat. No. 5,646,013), described supra, and the like.

In the preparation of the MEGF10-encoding vectors of the present invention the nucleic acid sequence encoding the MEGF10 protein, fragment or variant thereof is placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the m-actin promoter; and human growth hormone promoters. The promoter also may be the native promoter which controls the genes encoding MEGF10.

According to the present invention, there is provided a method for enhancing proliferation and/or inhibiting differentiation of a stem cell and/or a progenitor cell comprising, expressing MEGF10 or an active fragment or variant thereof in the stem cell.

According to an alternate embodiment, the present invention provides a method for inhibiting proliferation and/or enhancing differentiation of a cell comprising, expressing an inhibitor of MEGF10 protein production, comprising for example, but not limited to a MEGF10 antisense nucleic acid or siRNA in the cell.

The methods provided above optionally may include a prior step of selecting stem cells and/or one or more cells from a subject. In a preferred embodiment, the cells are satellite cells, myoblasts, pax7+/myf5− stem cells, pax7+/myf5+ progenitor cells or a combination thereof.

In a further embodiment, there is provided one or more antibodies against MEGF10 protein, a fragment or variant

EXAMPLES

Example 1

Experimental Procedures

Mice and animal care. ROSA26-LacZ (ROSA26R3) reporter mice, mdx mice carrying homologous mutated dystrophin gene, and CMV-Cre mouse strains were purchased from JaxMice (Jackson Laboratories, MI). The knock in Myf5–nlacZ (Tajbakhsh et al., 1996) heterozygous mice were directly used whereas, Myf5–Cre (Tallquist et al., 2000) heterozygous mice were bred with ROSA-YFP (Srinivas et al., 2001) or ROSA26R3 Cre reporter mice. Pax7-mutant mice carry the lacZ knock in mutation and were maintained in an in bred 129SV/J background (Kuang et al., 2006). All mice are maintained inside a barrier facility and experiments performed followed the University of Ottawa regulations for animal care and handlings.

Myofiber isolation and analysis. TA muscle from 6-8 week old Myf5–nLacz or Myf5-cre/ROSA26-YFP mice was injected with 25 μl CTX (10 μM, Latoxan, France). Four days later, the individual myofibers were isolated from the neighboring EDL muscle using a previously described fiber isolation procedure (Rosenblatt et al., 1995). An apical-basal division was defined such that each sister cell was in direct contact with either the apical or the basal boundaries of the satellite cells niche. Planar division was defined such that both daughter cells maintained direct contact with basal and apical boundaries. Isolated myofibers were either by plating in Matrigel-coated chamber slides, or cultured in suspension in 60-mm Petri dishes coated with horse serum to prevent fiber attachment (Kuang et al., 2006). Primary myoblasts were isolated from hindlimb muscles and cultured as previously reported (Megeney et al., 1996).

Histological and immunochemical analysis. Transplanted TA muscles were isolated, fixed in 4% paraformaldehyde (PFA), immersed in 30% sucrose in PBS for overnight, and embedded in OCT (Tissue-Tek) and cooled with isopentane on dry ice/ethanol mixture. Transverse sections (8 μm) of the muscle were cut with a cryostat (Leica CM1850). Immunochemical labeling of cryosections, myofibers and cells were performed at previously reported (Kuang et al., 2006). M.O.M. blocking kit (BMK-2202, Vector Lab) was used for staining of muscle sections prior to above-mentioned blocking. The primary antibodies used were listed in Table 1.

TABLE 1

List of antibodies used

| Antigen | Cat# | Supplier | Ig type | Dilution |
|---|---|---|---|---|
| For cell or tissue staining | | | | |
| Pax7 | Pax7 | DSHB (U Iowa) | Mouse IgG1 | 1:10 culture supernatant |
| GFP | A21311 | Invitrogen Molecular Probes | Rabbit IgG | 1:1000 |
| Laminin | L9393 | Sigma | Rabbit IgG | 1:1000 |
| Laminin-α2 | ALX-804-190 | Alexia Biochemicals | Rat IgG1 | 1:1000 |
| M-Cad | 611101 | BD transduction lab. | Mouse IgG2a | 1:500 |
| Dystrophin | AB15277 | Abcam | Rabbit IgG | 1:200 |
| NCAM | 5B8 | DSHB | Mouse IgG1 | 1:10 culture supernatant |
| AbcG | Ab24114 | Abcam | Rat IgG1 | 1:200 |
| c-Met | | Upstate | | 1:200 |
| Ki-67 | 550609 | BD Pharmingen | Mouse IgG1 | 1:250 |
| Phosphor-H3 | 06-570 | Upstate | Rabbit IgG | 1:500 |
| β1-Integrin | Ab5185 | Abcam | Rabbit IgG | 1:100 |
| α7-Integrin | K0046-3 | MBL international | Mouse IgG1 | 1:250 |
| CD34 | 553733 | BD Pharmingen | Rat IgG | 1:100 |
| Numb | Ab4147 | Abcam | Goat IgG | 1:500 |
| β-gal | A11132 | Invitrogen Molecular Probes | Rabbit IgG | 1:4000 |
| Syndecan-4 | | Dr. B. Olwin (U Colorado) | Chick IgG | 1:250 |

TABLE 1-continued

List of antibodies used

| Antigen | Cat# | Supplier | Ig type | Dilution |
|---|---|---|---|---|
| MyoD 5.8A | 13941A | BD Pharmingen | Mouse IgG1 | 1:500 |
| Myf5 C-20 | SC-302 | Santa Cruz | Rabbit IgG | 1:200 |
| MyHC | MF-20 | DSHB | Mouse IgG2b | 1:20 |
| Dystrophin | D8043 | Sigma | Mouse IgG1 | 1:500 |
| MyoD C-20 | SC-304 | Santa Cruz | Rabbit IgG | 1:200 |
| Primary Antibodies for FACS | | | | |
| α7-Integrin | K0046-3 | MBL international | Mouse IgG1 | 1:200 |
| CD45 | 01115A | BD Pharmingen | Rat IgG | 1:200 |
| Ter119 | 12-5921-82 | eBioscience | Rat IgG | 1:200 |
| Sca1-1 | 553336 | BD Pharmingen | Rat IgG | 1:200 |
| CD31 | 553373 | BD Pharmingen | Rat IgG | 1:200 |

The secondary antibodies used were Alexa488, Alexa568 and Alexa647 conjugated to specific IgG (Invitrogen Molecular Probes) that matched the primary antibodies (Invitrogen Molecular Probes). Zenon tricolor anti-Rabbit IgG labeling kit (Invitrogen Molecular Probes) and Avidin conjugated fluorophores were also used where applicable. Nuclei were counter stained with DAPI.

Cell sorting and PCR analysis. Mononucleated muscle derived cells were isolated from hind-limb muscles as previously described (Megeney et al., 1996), blocked with goat serum for 10 min at room temperature, incubated with primary antibodies in DMEM with 2% FBS and 10 mM HEPES at $1-3 \times 10^7$ cell/ml for 15 min at RT. Cells were briefly washed with the above DMEM solution and incubated with appropriate secondary antibodies (1:1000) at RT for 15 min. After staining, cells were washed with ice-cold DMEM, passed through 30 µm filters (Miltenyi Biotec) and suspended at a concentration of $1 \times 10^7$ cells/ml. Cells were separated on a MoFlo cytometer (DakoCytomation), equipped with 3 lasers. Sorting gates were strictly defined based on single antibody stained control cells. Dead cells and debris were excluded by PI staining, and by gating on forward and side scatter profiles. Total RNAs were prepared from $2 \times 10^4$ of sorted cell populations (expressing appropriate phenotypes) by TRIzol (GIBCO). cDNA synthesis and PCR were done as previously described (Minoguchi et al., 1997). Primers are listed in Table 2.

TABLE 2

Primer sequences for RT-PCR

| Gene | Sequence |
|---|---|
| Pax7 | 5'-GCTACCAGTACAGCCAGTATG-3' (SEQ ID NO: 3) <br> 5'-GTCACTAAGCATGGGTAGATG-3' (SEQ ID NO: 4) |
| Myf5 | 5'-TGAGGGAACAGGTGGAGAAC-3' (SEQ ID NO: 5) <br> 5'-GCAAAAGAACAGGCAGAGG-3' (SEQ ID NO: 6) |
| SA-YFP | 5'-CAAACTCTTCGCGGTCTTTC-3' (SEQ ID NO: 7) <br> 5'-AACAGCTCCTCGCCCTTG-3' (SEQ ID NO: 8) |

TABLE 2-continued

Primer sequences for RT-PCR

| Gene | Sequence |
|---|---|
| Cre | 5'-GCGGTCTGGCAGTAAAAACTATC-3' (SEQ ID NO: 9) <br> 5'-GTGAAACAGCATTGCTGTCACTT-3' (SEQ ID NO: 10) |
| β-Actin | 5'-AGCCATGTACGTAGCCATCC-3' (SEQ ID NO: 11) <br> 5'-CTCTCAGCTGTGGTGGTGAA-3' (SEQ ID NO: 12) |
| Notch-1 | 5'-TGAGACTGCCAAAGTGTTGC-3' (SEQ ID NO: 13) <br> 5'-GTGGGAGACAGAGTGGGTGT-3' (SEQ ID NO: 14) |
| Notch-2 | 5'-GCAGGAGCAGGAGGTGATAG-3' (SEQ ID NO: 15) <br> 5'-GCGTTTCTTGGACTCTCCAG-3' (SEQ ID NO: 16) |
| Notch-3 | 5'-GTCCAGAGGCCAAGAGACTG-3' (SEQ ID NO: 17) <br> 5'-CAGAAGGAGGCCAGCATAAG-3' (SEQ ID NO: 18) |
| Delta-1 | 5'-CCGGCTGAAGCTACAGAAAC-3' (SEQ ID NO: 19) <br> 5'-GAAAGTCCGCCTTCTTGTTG-3' (SEQ ID NO: 20) |
| Numb | 5'-CCGCACTAGAAAGCAAGTCC-3' (SEQ ID NO: 21) <br> 5'-ACAAAGTCCCCTTTGCTCCT-3' (SEQ ID NO: 22) |

Microscopy and live imaging analysis. Samples were visualized with a Zeiss Axioplan2 microscope and images acquired using a Zeiss AxioCam camera and the Axioview 3.1 software as previously described (Kuang et al., 2006). For clonal tracing of satellite cells, single myofiber cultures were monitored using a living imaging system. The system contains a Zeiss Axiovert 200 microscope equipped with an incubator (XL-3, Zeiss), a CO2 controller and a heating unit that maintain 37° C. and 5% CO2 within the incubator. Fluorescent and phase contrast images were recorded at 1 frame every 5 min using a 20× objective (LD Plan-Neofluar N. A. 0.4) with a Zeiss AxioCam and the AxioView 4.5 software.

Transplantation of sorted satellite cells. TA muscles of mdx mice were injected with 25 µl CTX (10 µM, Latoxan, France) 24 hrs prior to cell transplantation. For each injection, YFP+ cells and YFP–α7int+ cells isolated from Myf5–cre/ROSA-YFP mice were injected with 0.5 cc insulin syringes into the left and right TA muscle of the same mouse. For control experiments, TA muscle from mdx mouse were injected with either saline or CTX, and mock transfers performed. Injected mice were daily treated with immunosuppressant FK-506 (Fujisawa Pharmaceutical Co., Osaka, Japan) at a dose of 5 mg/Kg/d via i.p. injection (Kinoshita et al., 1994). For cell transplants into the TA muscle of 1-month-old Pax7–/– mice, the procedure was the same as described above, except that mice were neither CTX treated nor immunosuppressed.

Example 2

Satellite Cells are Heterogeneous by Myf5 Expression

Satellite cells uniformly express Pax7 (Seale et al., 2000), and also have been reported to express the Myf5–nLacZ knock-in allele in the quiescent sub-laminar state (Beauchamp et al., 2000). Without wishing to be bound by theory or limiting in any manner, it is possible that Myf5 transcription occurs in satellite cells that had undergone commitment to the myogenic lineage. Consequently, if satellite cells that did not express Myf5 could be detected, these would represent a candidate stem cell of the satellite cell compartment. Therefore, it was examined whether satellite cells uniformly express these markers on single myofiber preparations fixed immediately following isolation from EDL muscles of Myf5–nLacZ mice.

Figure 2:
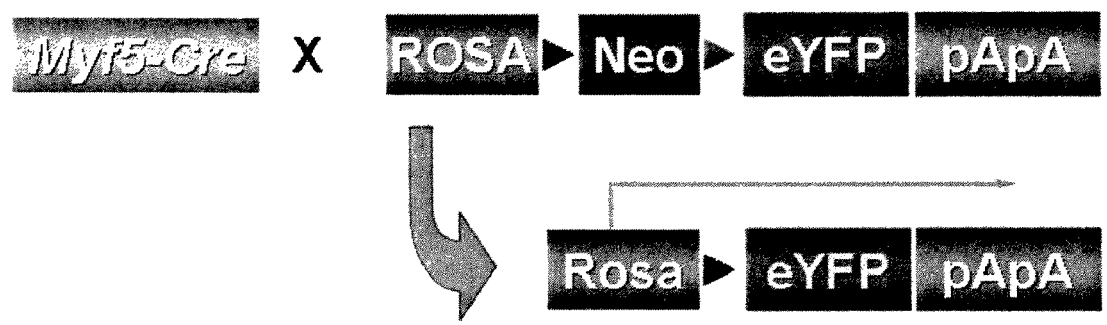
FIG. 2 is a schematic illustration of the Cre-LoxP system used in this study for genetic analysis of satellite cell lineage. In the absence of Cre recombinase, the expression of YFP is "stopped" by the Neo cassette that is flanked by LoxP sites (triangles). In the presence of Cre, recombination between the loxP sites results in the excision of the Neo cassette and subsequently the expression of YFP in cells that express ROSA26 gene. Under this system, all YFP expressing satellite cells must have expressed Myf5–Cre.

Immunohistological analysis revealed that the majority of satellite cells contained readily detectable levels of Pax7 and β-Gal proteins. Notably, 13±4% of Pax7-expressing satellite cells did not contain detectable levels of β-Gal suggesting that Myf5–nLacZ was not expressed (n=3 mice, >100 cells/mouse) (FIG. 1). However, it remained possible that the Pax7+/Myf5– cells were derived from satellite cells that had down-regulated Myf5. To investigate this possibility, genetic analysis using the Cre-LoxP system was employed to genetically mark cells that have expressed Myf5 by breeding heterozygous mice carrying a Myf5–cre knock in (Tallquist et al., 2000) with ROSA-YFP Cre reporter mice (Srinivas et al., 2001) (FIG. 2). In Myf5–cre/ROSAYFP mice, any satellite cells that had once expressed Myf5–cre should continue to express YFP (FIG. 2). To confirm the effectiveness of the Cre-LoxP system and expression of ROSA26 in satellite cells, the ROSA-YFP reporter mice were bred with CMV-cre transgenic mice that express Cre recombinase in the germline. As expected, in these animals YFP was expressed in 99.9% of Pax7-expressing satellite cells (n=3 mice, >100 cells/mouse).

Figure 3:
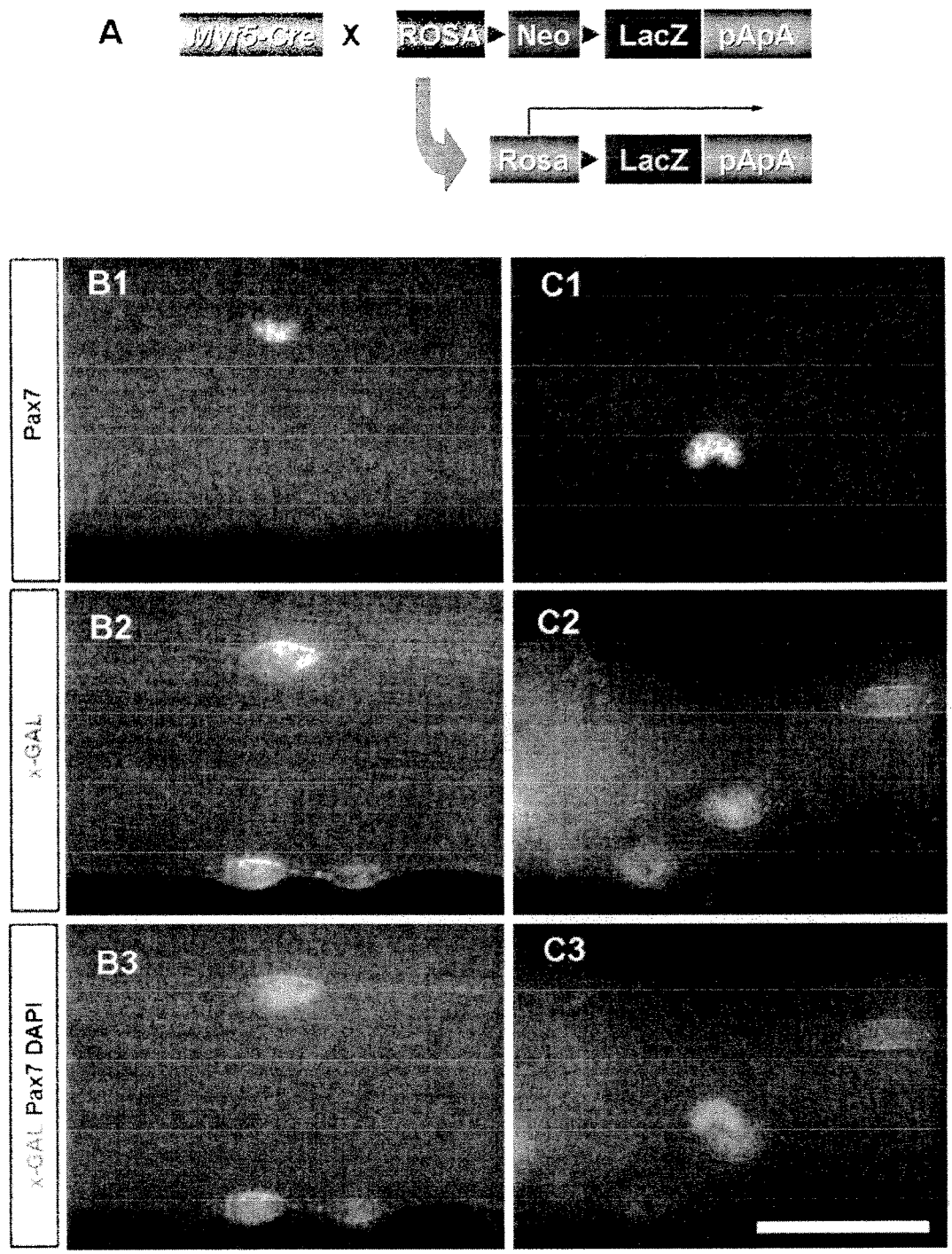
FIG. 3 shows satellite cell heterogeneity in muscle from the Myf5–Cre/ROSA26R3 reporter mouse.
Figure 4:
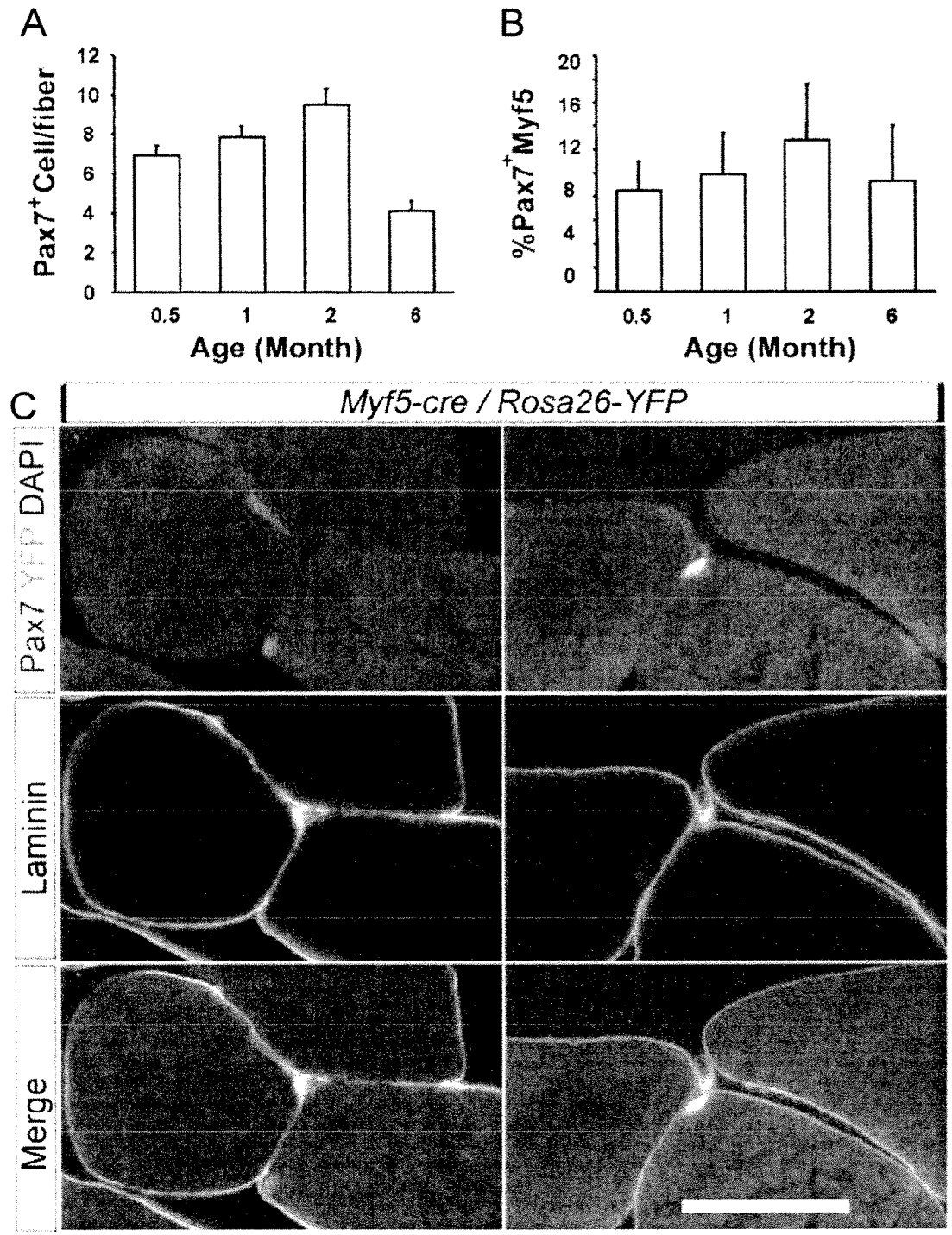
FIG. 4A shows the total number of Pax7+ satellite cells per EDL myofiber at different ages.
FIG. 4B shows the percentage of Pax7+/Myf5– satellite cells at different ages. In A and B, n=3, 4, 6, 3 mice for 0.5-, 1-, 2- and 6-month old mice, respectively).
FIG. 4C is a cross-section of TA muscle isolated from Myf5-Cre/ROSA-YFP reporter mice revealed the uniform sub-laminar localization of both Pax7+/Myf5– (left) and Pax7+/Myf5+ (right) cells. Scale bar: 25 μm in C.

Immunohistochemical analysis of myofibers isolated from Myf5–cre/ROSA-YFP EDL muscle was performed with anti-Pax7 and anti-GFP antibodies. Importantly, 90±2% of satellite cells expressing Pax7 also expressed YFP. However, 10±2% of Pax7+ satellite cells did not contain detectable levels of YFP suggesting that these cells have never expressed Myf5–cre (FIG. 1B; n=18 mice, >100 cells/mouse). Similar results were found after crossing Myf5–cre and ROSA26R3 reporter mice (FIG. 3). Interestingly, in 6-month-old mice the number of Pax7+ satellite cells per myofiber had declined (FIG. 4A), but the relative proportion of Pax7+/Myf5– satellite cells did not diminish (FIG. 4B). Furthermore, immunostaining of sectioned Myf5–cre/ROSA-YFP muscle with antibodies reactive with Pax7, YFP and laminin confirmed that the Pax7+/Myf5– cells were located beneath the basal lamina in a satellite cell position (FIG. 4C). Lastly, Pax7+/Myf5– satellite cells were found to express the satellite cell markers CD34, M-Cad, Syn4 and NCAM (FIG. 4D). Together, these genetic analyses indicate that Pax7+/Myf5– cells represent a subpopulation of sub-laminar satellite cells that have never expressed Myf5.

Example 3

Pax7+/Myf5– Cells Give Rise to Pax7+/Myf5+ Cells

Experiments indicated that about 10% of satellite cells in adult muscle have never expressed Myf5. These data therefore suggested that Myf5– satellite cells give rise to Myf5+ satellite cells. To investigate the developmental relationship between the Pax7+/Myf5– and Pax7+/Myf5+ cells, the clonal growth of satellite cells on isolated myofibers was examined in vitro, and developed a system to investigate satellite cell growth on muscle fibers in vivo.

Figure 6:
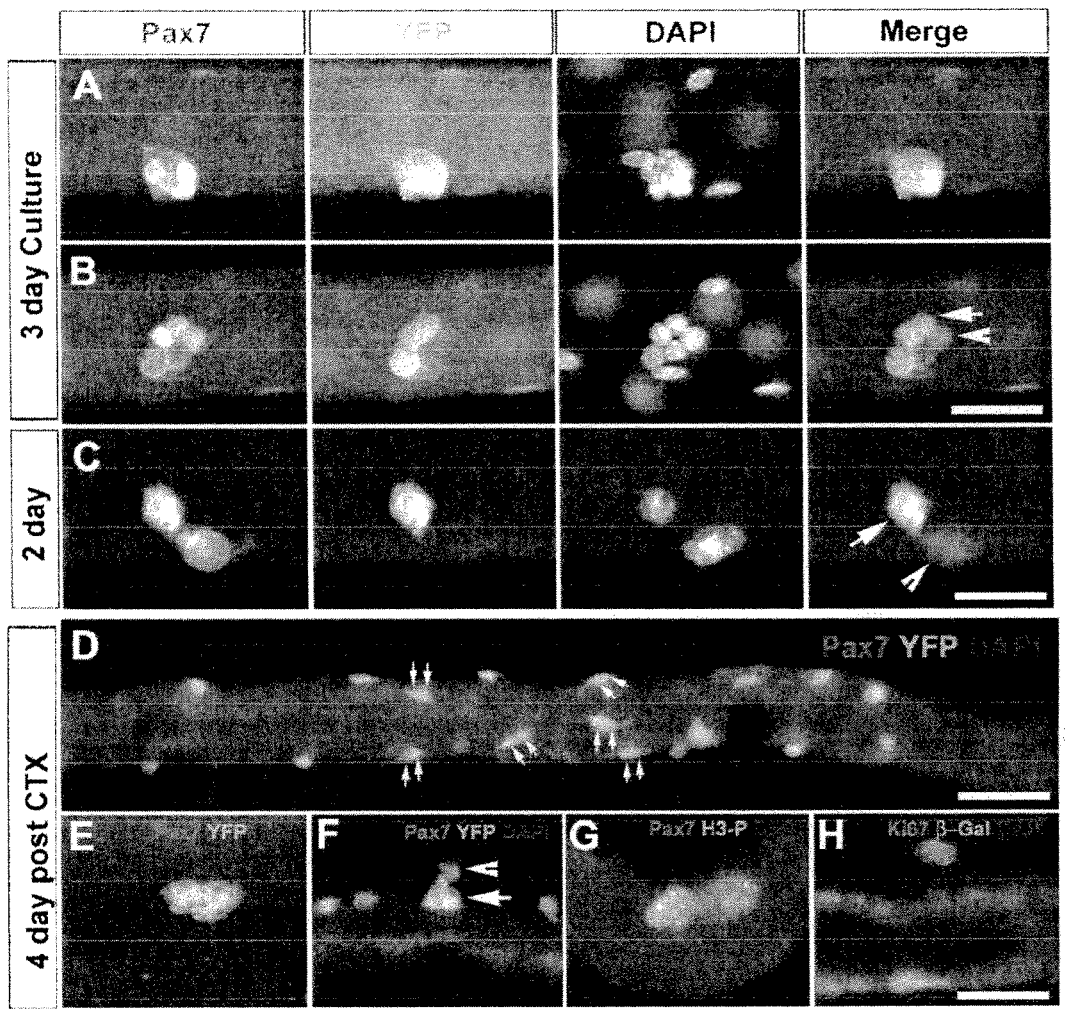
FIG. 6 shows the clonal growth of satellite cells implies a developmental relationship between Pax7+/Myf5– and Pax7+/Myf5+ satellite cells.

Individual myofibers were isolated from Myf5–Cre/ROSA-YFP EDL muscle and cultured in suspension under growth conditions for 1-3 days. Typically, satellite cells undergo their first cell division at around 24 h and form 4-8 cell aggregates within 3 d. Live imaging analysis confirmed that these aggregates were of clonal origin (not shown). Fixing and immunohistochemical detection for YFP and Pax7 revealed that by day 3 almost all clones uniformly expressed YFP. However, the level of Pax7 within each clone was variable (FIG. 6A). Importantly, about 10% of the clones contained both Pax7+/YFP– and Pax7+/YFP+ cells at day 3 (FIG. 6B) and day 2 (FIG. 6C) of culture (4 out of 41 clones from 3 experiments). These data therefore indicate that a developmental relationship exists between Pax7+/Myf5– and Pax7+/Myf5+ satellite cells.

To examine satellite cell divisions within the satellite cell niche in vivo, a novel approach to analyze satellite cell proliferation was developed. Typically, induction of muscle injury with cardiotoxin (CTX) results in death of myofibers (Megeney et al., 1996). Therefore, for these experiments fibers from the adjacent EDL muscle were isolated 4-5 days following cardiotoxin injection into the TA muscle. It was found that this approach resulted in activation of satellite cells without the death of the myofiber in the EDL muscle (FIG. 6D), presumably due to reduced exposure to CTX.

Proliferating satellite cells associated with single fibers did not form large clones of sphere-like cells in vivo, but numerous doublets of sister cells (double arrows in FIG. 6D) were observed on viable regenerating fibers which contained long arrays of centrally located nuclei (FIG. 6D). The vast majority of the doublets displayed identical expression of Pax7 and Myf5 (FIG. 6E). Nonetheless, we identified doublets of proliferating cells with one Pax7+/Myf5– and one Pax7+/Myf5+ cells (FIG. 6F), on regenerating fibers from both Myf5–Cre/ROSA-YFP double transgenic and Myf5–nLacZ reporter mice. The clonal origin of these doublet sister cells was confirmed by their physical proximity, the expression of proliferation markers in both cells (Ki67 and phospho-H3; FIGS. 6G, H), and their sub-laminar localization within the same satellite cell niche (Refer to FIGS. 8C, D).

Figure 7:
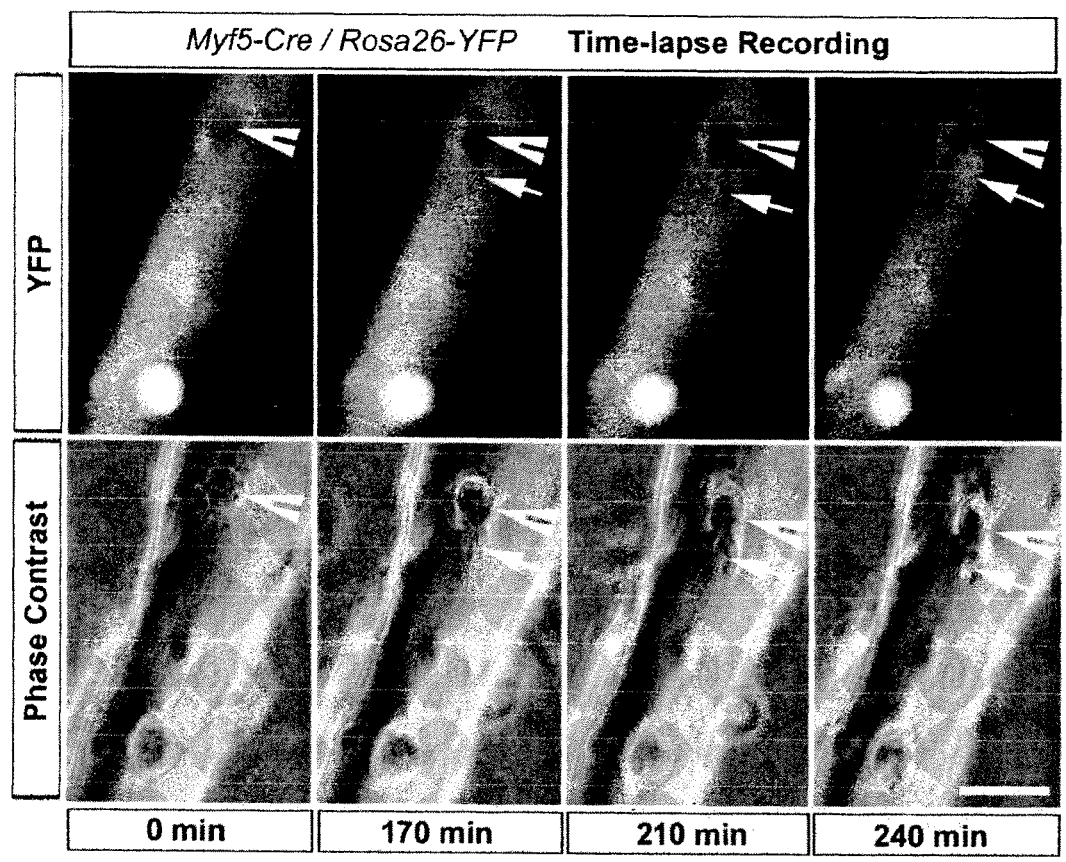
FIG. 7 shows that Pax7+/Myf5– cells give rise to Pax7+/Myf5+ cells. Time-lapse imaging analysis revealed that a YFP– satellite cell (arrowhead at T=0) on an individual myofiber isolated from the EDL muscle from Myf5–Cre/ROSA-YFP reporter mouse gave rise to YFP– (arrowheads) and YFP+ daughter (arrows) cells after cell division. Cell division occurred at approximately 0 min and YFP expression became apparent in the lower daughter cell at 240 min. Scale bar: 25 μm.

Finally, time-lapse imaging analysis of satellite cell division on cultured single myofibers isolated from Myf5–Cre/ROSA-YFP double transgenic mice was conducted. It was observed that single YFP– satellite cells give rise to one YFP– and one YFP+ cell (FIG. 7). Altogether, these results unequivocally demonstrate that Pax7+/Myf5– cells give rise to Pax7+/Myf5+ cells upon asymmetric cell division, and further suggest that Pax7+/Myf5− cells represent a stem cell reservoir that maintains a hierarchical composition of the satellite cell compartment by means of asymmetric cell divisions.

Example 4

Satellite Cell Asymmetric Division Mediates Self-Renewal and Differentiation

Figure 8:
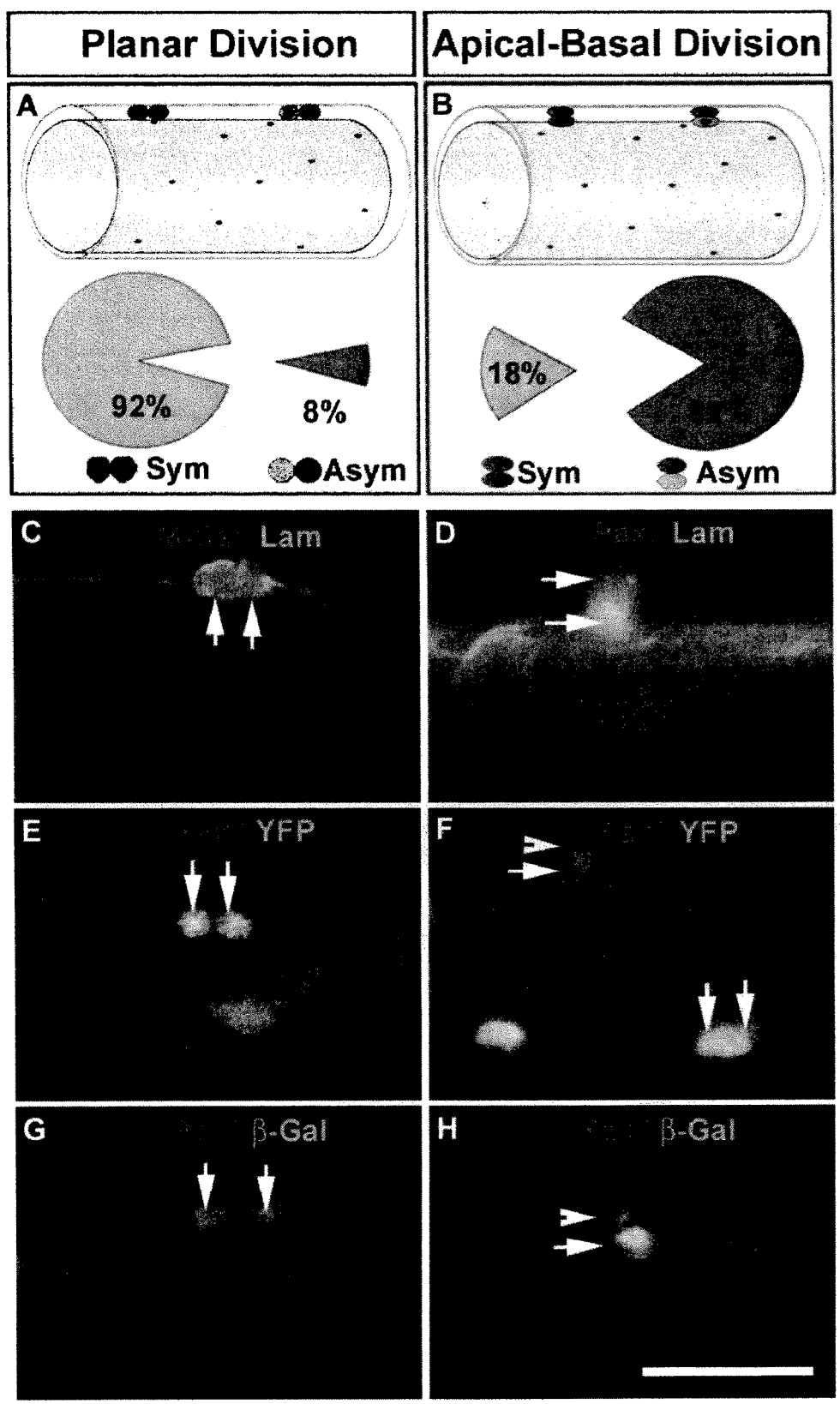
FIG. 8 shows that the orientation of the mitotic spindle within the satellite cell niche determines symmetry of cell division.

Given that a single Pax7+/Myf5− cells give rise to both Pax7+/Myf5− and Pax7+/Myf5+ daughter cells through apparent asymmetric cell divisions, the correlation of the orientation of cell division with the fate of daughter cells (Fuchs et al., 2004) was investigated. The Pax7 and Myf5−nLacZ or Myf5−cre/ROSA-YFP expression of newly divided sister satellite cells was analyzed in the context of their positioning relative to the basal lamina in regenerating EDL muscle as described above (FIG. 8A-B). Examination of myofibers isolated from regenerating EDL muscle revealed doublets of sister satellite cells uniformly beneath the basal lamina (FIGS. 8C, D), in both planar and apicalbasal orientations relative to the basal lamina (FIG. 8C-H). Doublets of cells within the satellite cell niche were predominantly planar in an orientation parallel to the basal lamina. Planar divisions almost exclusively gave rise to identical daughter cells (92%, n=89 pairs) that were both either Pax7+/Myf5−, or Pax7+/Myf5+ (FIGS. 8A, E, G). This phenomenon was documented in Myf5−cre/ROSA-YFP (FIG. 8E) and Myf5−nLacZ reporter muscles (FIG. 8G). Strikingly, we also observed asymmetric cell divisions (82%, n=38 pairs) that occurred in an apical-basal orientation at a right angle to the plane of the basal lamina (FIG. 8B). The majority of doublets in an apical-basal orientation revealed that Pax7+/Myf5− cell remained against the basal surface and the Pax7+/Myf5+ cell located on the apical side against the muscle fiber (FIGS. 8F, H). In addition, rare events where the basal cell expressed Pax7 and Myf5, and the apical cell had down regulated Pax7 and was presumably undergoing terminal differentiation (not shown) were observed.

Figure 9:
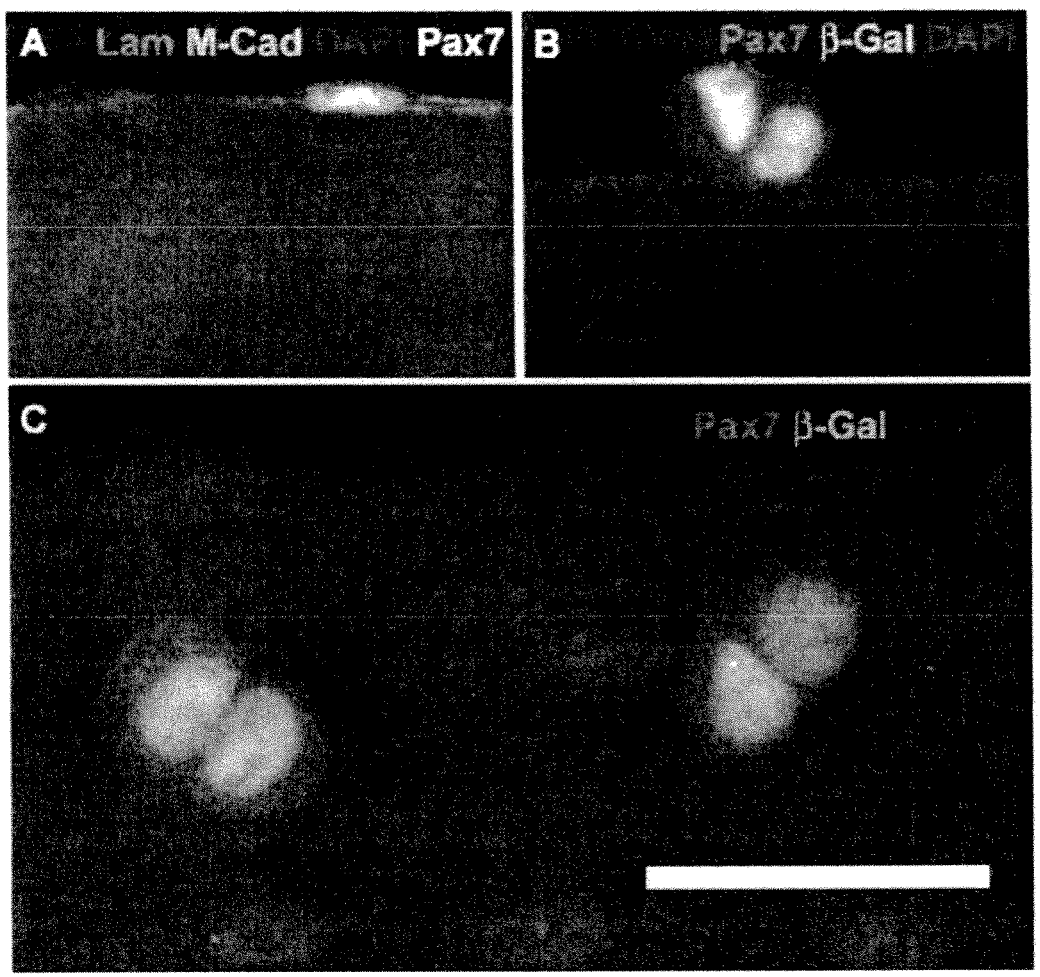
FIG. 9 shows symmetric and asymmetric division of satellite cells in vitro.

In parallel, satellite cells on myofibers cultured in suspension exhibited an analogous phenomenon but in an inverse orientation relative to the basal lamina (FIG. 9). In culture, prior to cell division, satellite cells translocated to the outside surface of the basal lamina, and maintained M-Cad expression at the apical surface away from the basal lamina (FIG. 9A). Planar-oriented cell divisions outside of the basal lamina typically gave rise to identical daughter cells. In asymmetric cell divisions, the Pax7+/Myf5− cells typically remained against the basal lamina on the outside surface, and the Pax7+/Myf5+ daughter cell were located apically away from the fiber (FIGS. 9B, C). Without wishing to be bound by theory or limiting in any manner, it was concluded that in vitro culture of myofibers leads to a disruption of the satellite cell niche, and presumably to a loss of the physiological inputs that normally regulate satellite cell function.

Together, these in vivo and in vitro analyses indicate that skeletal muscle satellite cell pool is composed of a hierarchy of cells at different developmental stages. Pax7+/Myf5− cells undergo self-renewal and give rise to Pax7+/Myf5+ cells through apical-basal asymmetric divisions, or exclusively self renew through planar symmetric divisions. These results strongly support the assertion that satellite cells are a heterogeneous population composed of stem cells and committed progenitors.

Example 5

Isolation and Characterization of Pax7+/Myf5− and Pax7+/Myf5+ Satellite Cells

Figure 10:
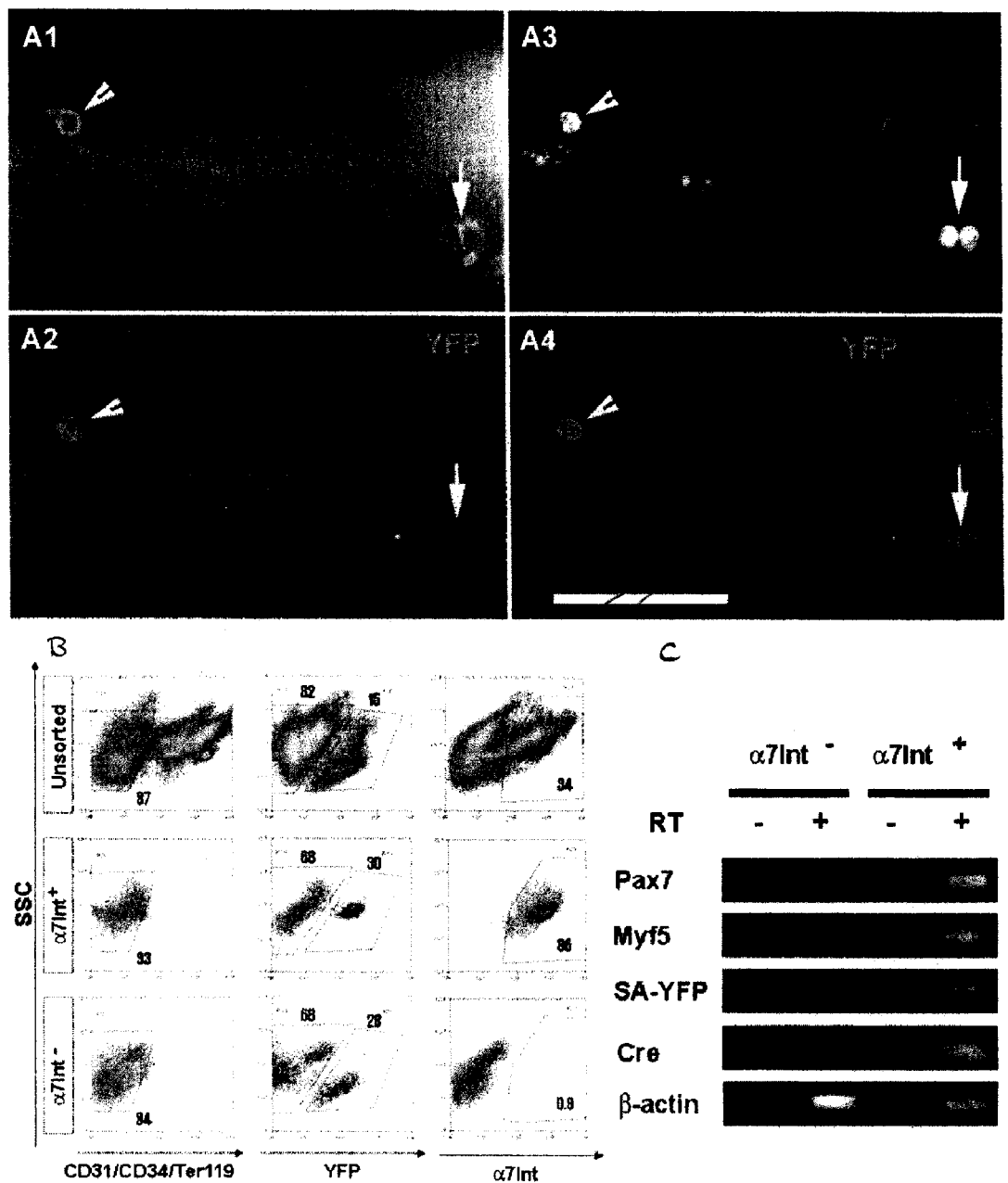
FIG. 10 shows prospective isolation Pax7+/Myf5– and Pax7+/Myf5+ satellite cells.

To further characterize Pax7+/Myf5− and Pax7+/Myf5+ satellite cells, a method to prospectively isolate the different satellite cell subpopulations was developed. Previously, purification of highly purified populations of primary myoblasts has been reported using antibody reactive with the cell surface protein α7-integrin and fluorescence activated cell sorting (FACS) (Blanco-Bose et al., 2001). Immunohistological analysis of isolated myofibers confirmed that α7-integrin was expressed on both Pax7+/Myf5− and Pax7+/Myf5+ satellite cells (FIG. 10A). Therefore, we employed positive selection for α7-integrin, together with negative selection for Sca1, CD31, CD45 and Ter119 (to remove endothelial and other non muscle cell types, FIG. 10B left column).

Figure 5:
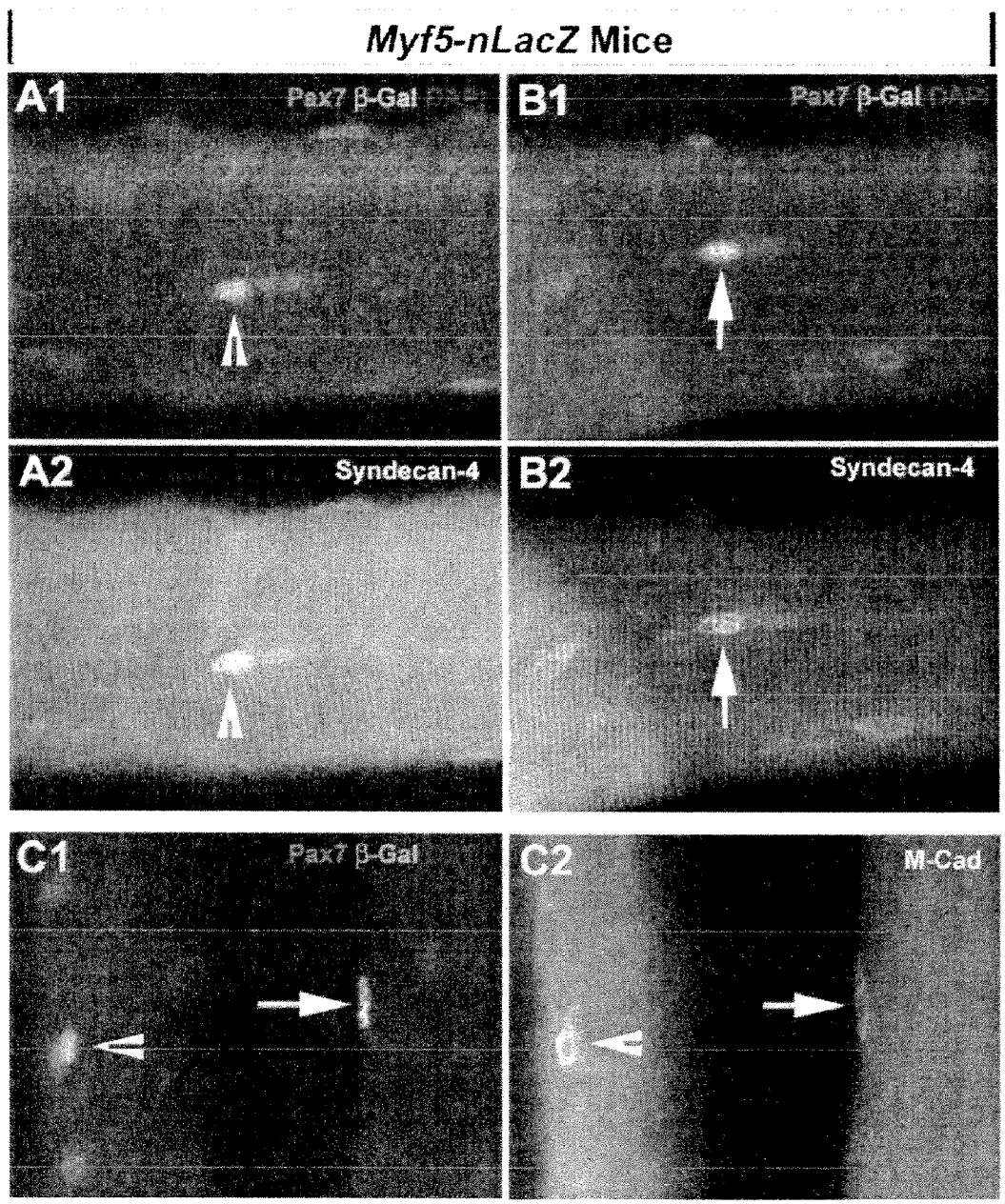
FIG. 5 shows Pax7+/Myf5– and Pax7+/Myf5+ satellite cells similarly express Syn4, M-Cad, NCAM and CD34.
Figure 5:
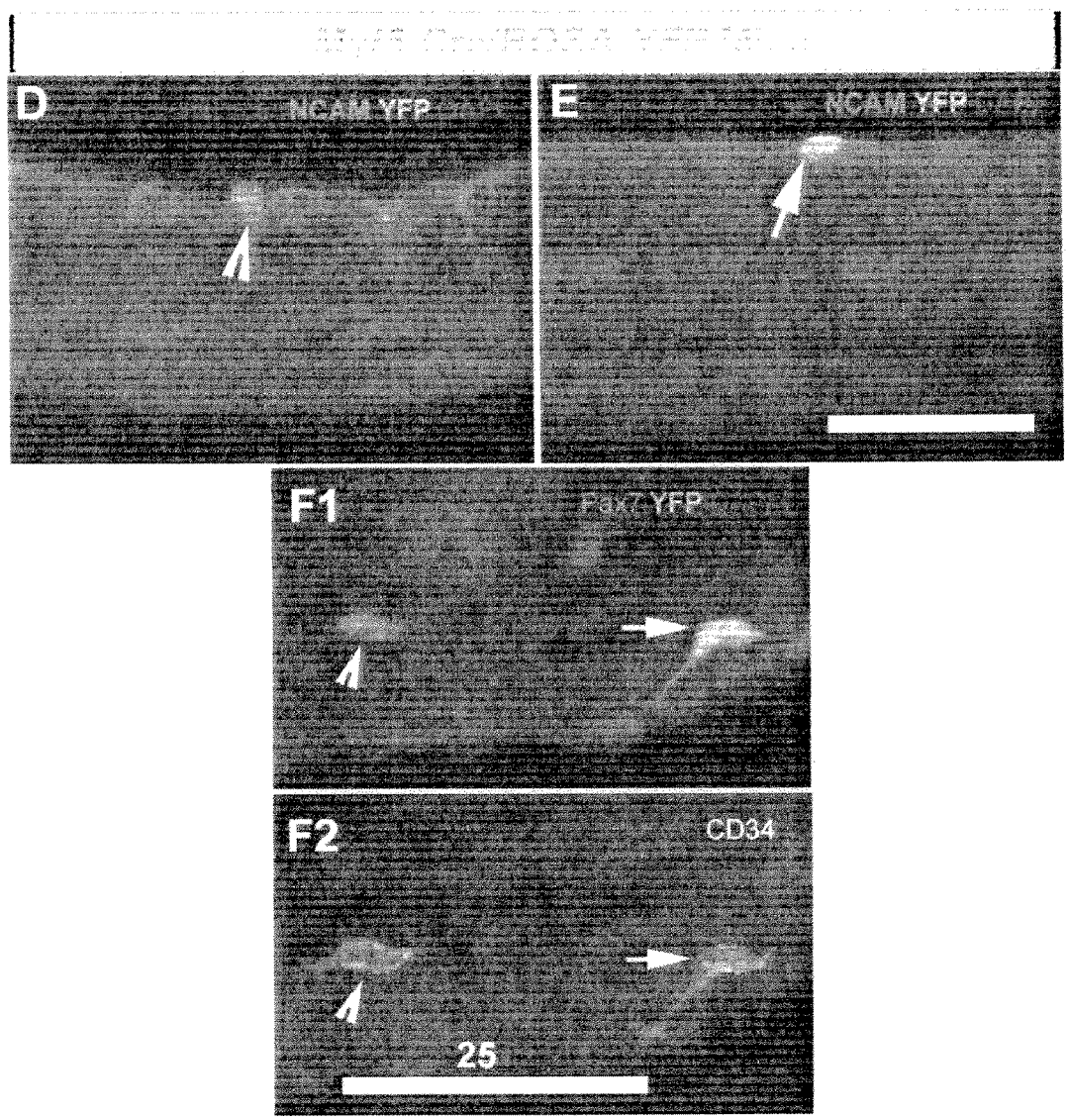
Figure 11:
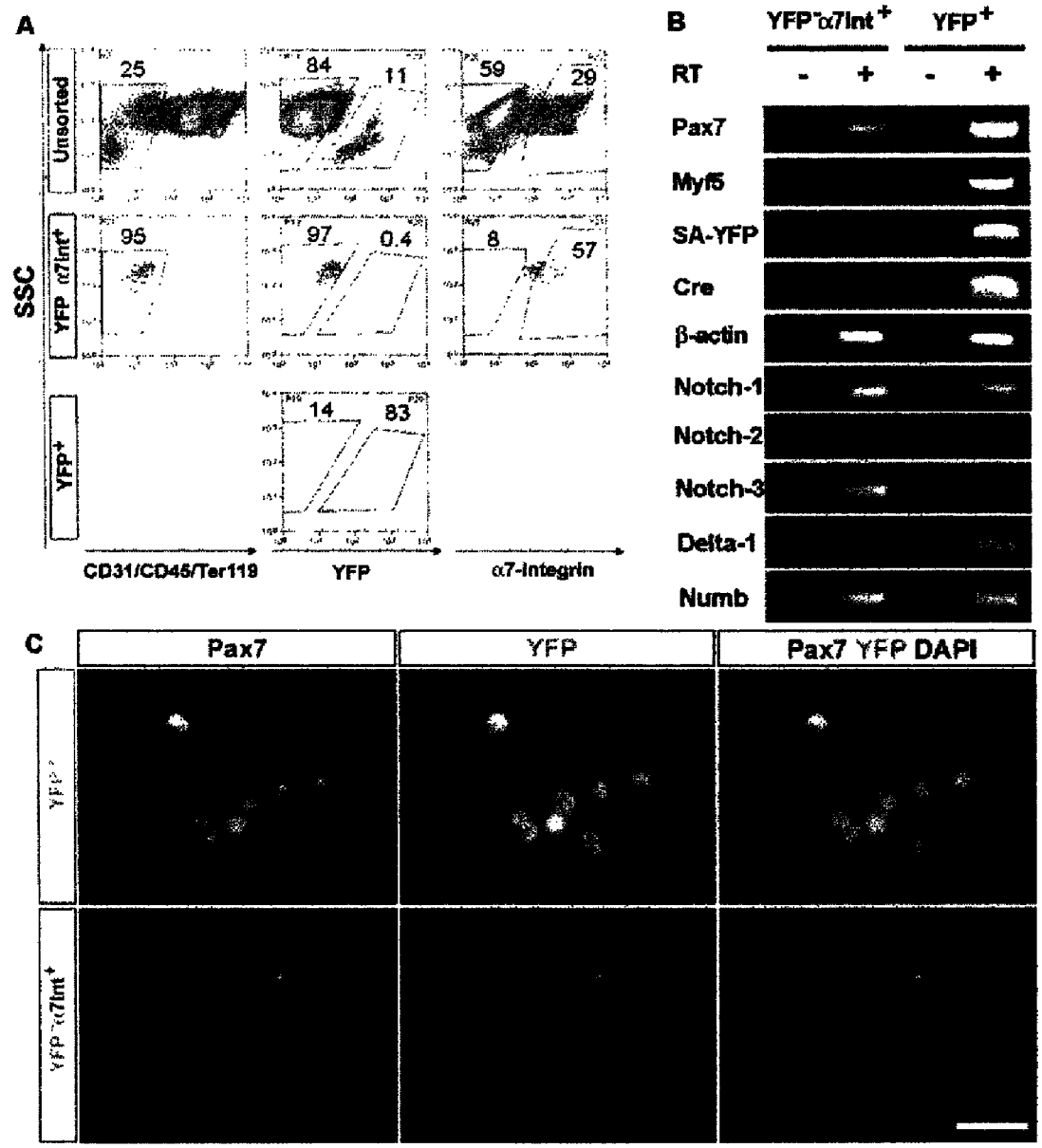
FIG. 11 shows isolation, and gene expression profile of Pax7+/Myf5– and Pax7+/Myf5+ satellite cells.

Mononuclear cells were isolated from Myf5−cre/ROSA26-YFP muscle and cells stained with antibodies reactive with α7-integrin, CD31, CD45 and Ter119. FACS analysis revealed that the α7-integrin stained fraction contained both YFP+ and YFP− cells (FIG. 10B, right column). RT-PCR analysis indicated that mRNA for Pax7, Myf5 and Cre were only present in the α7-integrin expressing fraction (FIG. 1C). Next, the YFP+ and the YFP−/α7-integrin+/Sca1−/CD31−/CD45−/Ter119-(termed "YFP−α7int+" hereafter) cells were isolated by FACS (FIG. 11A). RT-PCR analysis of YFP+ cells confirmed expression of Pax7, Myf5, Cre and SA-YFP mRNAs. By contrast, YFP−α7int+ cells expressed lower levels of Pax7 and did not express Myf5, Cre or SA-YFP (FIG. 5B). Occasionally extremely low level of Myf5 was detected in some YFP−α7int+ fractions, possibly reflecting gene activation during cell preparation.

Since Notch signalling is involved in the regulation of myogenic differentiation, the expression of Notch family genes was also examined in FACS purified fractions. Strikingly, the Notch ligand Delta-1 gene was only expressed in the YFP+ faction but not in the YFP−α7int+fraction (FIG. 11B). Other genes in the Notch family, Notch-1 and Notch-2 receptors and the Notch signalling inhibitor Numb, are equally expressed by both fractions, whereas Notch-3 was high in the YFP−α7int+faction but low in the YFP+ fraction. Without wishing ton be limiting or bound by theory in any manner, these results suggest that Notch signalling plays a positive role in the maintenance of Pax7+/YFP− satellite cells in an undifferentiated stem cell state through an inhibitory mechanism (Delfini et al., 2000).

To assess the efficiency of cell purification, freshly sorted cells were immunostained with antibody reactive to Pax7 following attachment to culture slides (FIG. 11C). Overall, 89±6% of the cells from YFP+ fraction expressed detectable levels of Pax7 (n=4), and 20±5% of cells from the YFP−α7int+ fraction expressed Pax7 (n=4). Therefore, FACS-purification of YFP−α7int+ cells provided a population significantly enriched in Pax7+/YFP− satellite cells.

Example 6

Figure 12:
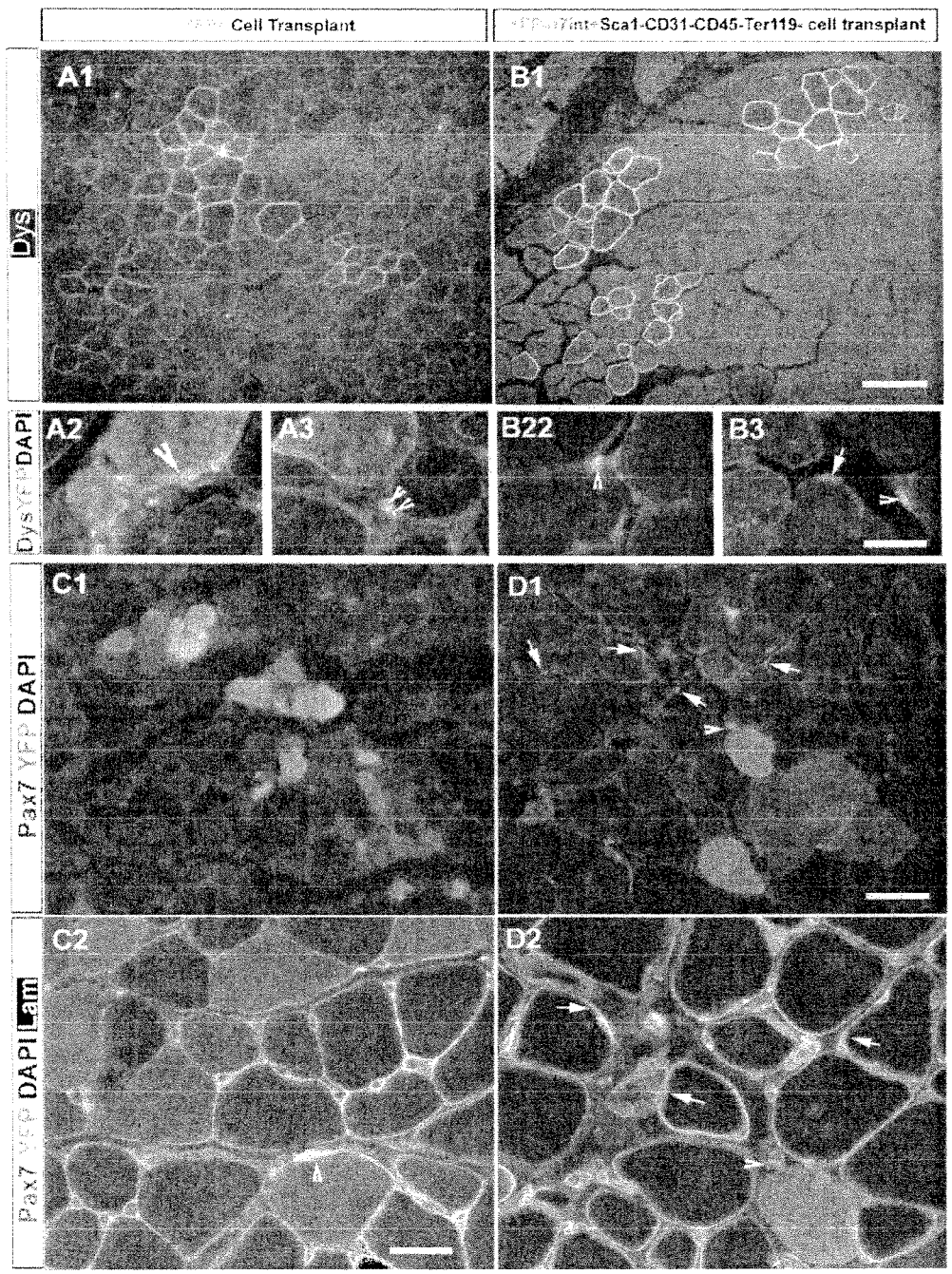
FIG. 12 shows that transplanted Pax7+/Myf5– cells extensively contribute to the satellite cell compartment.

Transplanted Pax7+/Myf5− Cells Extensively Contribute to the Satellite Cell Compartment Experiments suggested that satellite cells are a heterogeneous population composed of Pax7+/Myf5− stem cells and Pax7+/Myf5+ committed progenitors. To examine the biological function of these two subpopulations of satellite cells, 2,400-10,000 FACS purified YFP+ and YFP−α7int+ cells were transplanted into skeletal muscle of mdx mice, to assess participation in fibrogenesis, and into Pax7−/− muscle to assess contribution to the satellite cell compartment. First, FACS-purified YFP+ and YFP−α7int+ satellite cells were injected into regenerating TA muscles of mdx mice at 24 hrs following CTX-induced injury. Remarkably, muscles grafted with YFP−α7int+ satellite cells contained more dystrophin-expressing myofibers and displayed more intense dystrophin expression (FIG. 12A-B). Injection of YFP+ satellite cells generated 28±9 fibers expressing dystrophin per TA muscle per 1,000 transplanted Pax7+ cells (n=3 mice, 3 section/mouse). However, injection of YFP−α7int+ satellite cells generated 146±48 fibers expressing dystrophin per TA muscle per 1,000 transplanted Pax7+ cells (n=3 mice, 3 section/mouse). By contrast, in control mock injection and non-treatment experiments we observed 9±1 revertant dystrophin positive myofibers per TA (n=2 mice). Therefore, it was concluded that the Pax7+/Myf5− subpopulation of satellite cells were approximately 5-fold more effective at restoring dystrophin expression as the Pax7+/Myf5+ subpopulation.

Transplantation of FACS-purified YFP+ and YFP−α7int+ satellite cells into undamaged TA muscle of mdx mice revealed different behaviors of these two subpopulations. YFP+ satellite cells were observed to remain at the injection site and preferentially fuse with each other to form clusters of YFP+ myofibers in the host muscle (FIG. 12A2). Rare mononuclear YFP+ cells were found in the interstitial environment (FIG. 12A3) or associated with donor-derived YFP+ myofibers (FIG. 12A2), but were never found to occupy a satellite cell position in host myofibers. By contrast, transplantation of YFP−α7int+ satellite cells preferentially gave rise to sub-laminar satellite cells, including donor derived YFP−/dystrophin+ and YFP+/dystrophin+ satellite cells (FIG. 12B2-3). Only rare YFP+/Dystrophin+ cells were found within the interstitial spaces.

To further investigate the ability of Pax7+/Myf5− versus Pax7+/Myf5+ satellite cells to contribute to the satellite cell compartment, FACS-purified cells were transplanted into the TA muscle of Pax7−/− mice. Notably, Pax7-deficient mice lack functional satellite cells and therefore the satellite cell niche is accessible to the transplanted cells. Immunohistochemical analysis of the TA muscle was performed 20 days following transplantation with antibody reactive to Pax7 and YFP.

Figure 13:
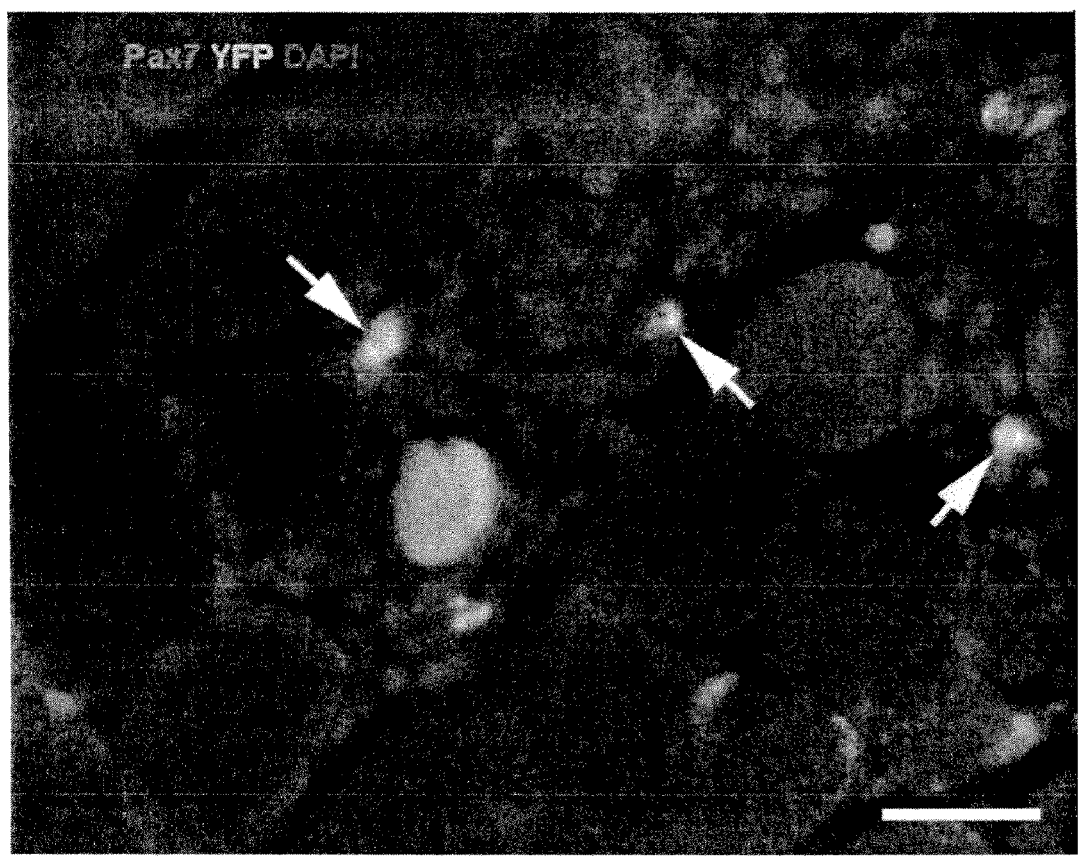
FIG. 13 shows interstitial mononuclear Pax7+/YFP+ cells (arrows) 20 day after transplantation of FACS isolated YFP+ cells into Pax7 mutant mouse. The YFP+ cells were isolated from Myf5–Cre/ROSA-YFP transgenic mouse. Note the numerous nuclei surrounding a YFP+ myofiber indicative of host immunoresponse. Scale bar: 25 µm.

Following transplantation of YFP+ satellite cells into TA muscles of the Pax7−/− recipients, the donor cells formed clusters of myofibers expressing high levels of YFP suggesting the cells had fused with one another (FIG. 12C1). Transplanted YFP+ cells did not give rise to YFPsatellite cells. However, we observed rare YFP+ satellite cells associated with the newly fused myofiber (FIG. 12C2), as well as mononuclear YFP+ cells in interstitial spaces between fibers (FIG. 13). YFP+ cells were never observed to occupy the sub-laminar satellite cell niche on host myofibers. By contrast, after transplantation of YFP−α7int+ satellite cells into the TA muscles of the Pax7−/− recipients, numerous Pax7+/YFP− and Pax7+/YFP+ cells located in a sublaminar position on host myofibers and fewer YFP+ myofibers were observed (FIG. 12D). Specifically, injection of YFP+ satellite cells generated 0.5±0.5 sub-laminar YFP+ satellite cells per microscopic field near the injection sites (20×, ~0.1 mm2) per 10,000 transplanted Pax7+ cells (n=3 mice, 2-8 field/mouse). Moreover, these cells were associated with YFP+ fibers formed near the injection site. By contrast, injection of equal numbers of YFP−α7int+ satellite cells generated 5.8±4.6 sub-laminar satellite cells per field near the injection sites (n=3 mice, 2-6 field/mouse). These cells were found associated with host fibers throughout the belly of the injected muscle with higher occurrence near the center of injection. Together, these data indicate that transplanted Pax7+/Myf5+ satellite cells preferentially undergo terminal differentiation whereas transplanted Pax7+/Myf5− satellite cells extensively contribute to the satellite compartment and give rise to both classes of satellite cells. Therefore, it was concluded that satellite cells are a heterogeneous population composed of Pax7+/Myf5− stem cells and Pax7+/Myf5+ committed progenitors.

It had been previously shown that satellite cells uniformly express the transcription factor Pax7 (Seale et al., 2000). Using a Myf5−Cre knock in allele and a ROSA-YFP Cre reporter, it was observed in the above experiments that in vivo about 10% of satellite cells express Pax7 but have never expressed Myf5. Moreover, it was found that Pax7+/Myf5− satellite cells give rise to Pax7+/Myf5+ satellite cells through basal-apical asymmetric cell divisions. Prospective isolation followed by transplantation confirmed that Pax7+/Myf5+ satellite cells preferentially differentiate, whereas Pax7+/Myf5− satellite cells extensively contribute to the satellite cell compartment. These data therefore indicate that sub-laminar satellite cells in skeletal muscle are a heterogeneous population composed of stem cells (Pax7+/Myf5−) and committed myogenic progenitors (Pax7+/Myf5+). This discovery provides a new paradigm that redefines satellite cell biology and opens new doors for therapeutic intervention for the treatment of devastating neuromuscular diseases, for example, but not limited to Duchene Muscular Dystrophy (DMD), Becker muscular dystrophy (BMD), myotonic dystrophy (also known as Steinert's disease), limb-girdle muscular dystrophies, facioscapulohumeral muscular dystrophy (FSH), congenital muscular dystrophies, oculopharyngeal muscular dystrophy (OPMD), distal muscular dystrophies and Emery-Dreifuss muscular dystrophy.

Satellite cells express several markers including Pax7 (Seale et al., 2000), Vascular Cell Adhesion Molecule 1 (VCAM-1) (Rosen et al., 1992), c-met (receptor for HGF), M-cadherin protein (Cornelison and Wold, 1997; Irintchev et al., 1994), Neural Cell Adhesion Molecule 1 (NCAM1) (Bischoff, 1994), Foxk1 (Garry et al., 1997), CD34 (Beauchamp et al., 2000), Myf5 (Beauchamp et al., 2000), and Syndecans 3 and 4 (Cornelison et al., 2001). However, expression of several of these markers has been noted to be heterogeneous. For example, Beauchamp and coworkers noted heterogeneity in expression of CD34, Myf5, and M-cadherin in satellite cells and hypothesized that CD34+/Myf5+/Mcad+ expression defined a quiescent, committed precursor and that the CD34−/Myf5− minority were involved in maintaining the lineage-committed majority (Beauchamp et al., 2000). Examination of satellite cell growth on cultured myofibers suggested that activated satellite cells synchronously activated Pax7 and MyoD, then either proliferate, down-regulate Pax7, and differentiate, or alternatively become quiescent and down-regulate MyoD and maintain Pax7 (Zammit et al., 2004). These data were interpreted as suggesting satellite cells were derived from de-differentiated myoblasts. Ectopic expression studies have suggested that Pax7 plays a role in allowing satellite cells to reacquire a quiescent, undifferentiated state (Olguin and Olwin, 2004), whereas other studies have suggested that Pax7 maintains proliferation and prevents differentiation, but does not promote quiescence (Zammit et al., 2006).

Without wishing to be bound by theory, the present findings support the assertion that Pax7 expression defines the stem cell state, whereas co-expression of Pax7 and Myf5 defines myogenic commitment. Both populations express CD34 and other satellite cell markers, and readily divide in vivo within the sub-laminar satellite cell niche during muscle regeneration. Therefore, the present experiments do not support the notion that Myf5 expression defines satellite cell activation, or entry into the cell cycle. Rather, they support the assertion that a hierarchal developmental relationship exists between Pax7-expressing satellite stem cells, and Pax7 and Myf5 co-expressing committed satellite myogenic progenitor cells.

Previous studies have suggested that the satellite cells are not a homogeneous population. Radioisotope labeling of growing rat muscle demonstrated that satellite cells are a 4:1 mix of fast- and slow-cycling cells (Schultz, 1996). Transplantation of cultured primary myoblasts is unable to efficiently contribute to the satellite cell pool (Collins et al., 2005; Cousins et al., 2004; Heslop et al., 2001). However, direct transplantation of freshly isolated satellite cells revealed that some portion of these cells could give rise to additional satellite cells (Montarras et al., 2005). In addition, Collins and co-workers elegantly demonstrated that transplantation of a single myofiber into regenerating muscle of mdx mice not only resulted in robust muscle regeneration, but more importantly the re-population of the satellite cell pool that was previously depleted by irradiation (Collins et al., 2005). Together, these studies suggest that the satellite cell compartment is composed of at least two subpopulations, a fast-cycling cell committed to differentiate, and a slow-cycling cell capable of maintaining the overall satellite cell population. The present findings are consistent with this body of work and demonstrate that about 10% of sub-laminar satellite cells represent a stem cell reservoir, whereas the remainders are committed myogenic progenitors.

In studies of mdx mice, a mouse model of human DMD, it has been noted that a radioresistant subpopulation of satellite cells is depleted relative to wild type muscle (Heslop et al., 2000). Moreover, satellite cell derived myoblasts display accelerated differentiation kinetics when isolated from mdx mice (Yablonka-Reuveni and Anderson, 2006). These data suggest that in the absence of dystrophin, the equilibrium between stem cells and committed progenitors within the satellite cell compartment is perturbed. Without wishing to be bound by theory, the maintenance of the satellite stem cell pool is diminished and that this phenomenon may contribute to the progression and severity of DMD.

Recent advances have provided important insights into the role played by the microenvironment in regulating stem cell function (Fuchs et al., 2004). The stem cell niche directs the maintenance of stem cell identity, as well as the asymmetric generation and issue of committed daughter cells from the niche. Cell polarity has been hypothesized to be established within the stem cell niche by cell-cell interactions mediated by cadherins, and cell-extracellular matrix interactions mediated by integrins (Fuchs et al., 2004). Stem cell polarity and spindle orientation relative to the basal lamina determines whether a stem cell division will be symmetric or asymmetric. Planar divisions are symmetrical and generate identical daughter cells. By contrast, apical-basal divisions are asymmetric with one daughter cell remaining a stem cell at the basal surface, and a committed daughter cell destined for differentiation on the apical surface (Fuchs et al., 2004; Lechler and Fuchs, 2005). Therefore, the discovery of the stem cell niche provides an anatomical means to establish the identity of a stem cell population within a particular tissue.

Muscle satellite cells occupy a niche featuring a structural foundation for asymmetric self-renewal. The basal side of satellite cell is covered by the basal lamina ensheathing the muscle fiber, while the apical side of satellite cell is adjacent to the myofiber. The laminin receptor $\alpha7\beta1$ integrin is specifically expressed in satellite cells on the basal surface, whereas the cell adhesion molecule M-cadherin is specifically expressed on the apical surface towards the muscle fiber (Bornemann and Schmalbruch, 1994; Burkin and Kaufman, 1999; Collo et al., 1993; Irintchev et al., 1994).

The above data documents the generation of Pax7+/Myf5+ cells from a Pax7+/Myf5− cells by apical-basal asymmetric cell divisions within the satellite cell niche. Isolation and transplantation of the satellite cell subpopulations confirmed that Pax7+/Myf5+ cells preferentially differentiate whereas Pax7+/Myf5− cells can extensively contribute to the satellite cell compartment. Therefore, anatomical and functional experiments provide compelling evidence that the satellite cell population is composed of hierarchal subpopulations of stem cells and committed myogenic progenitors.

Asymmetric self-renewal of the satellite cell compartment was first postulated by Schultz (1996), and has been recently supported by the observation of asymmetric cell divisions and distribution of Numb in satellite cell derived daughter cells in culture (Conboy and Rando, 2002). Furthermore, during early embryonic myogenesis in chick, apical-basal oriented division of muscle progenitor cells is associated with asymmetric distribution of Numb to the basal side of dividing cells (Holowacz et al., 2006; Venters and Ordahl, 2005). Finally, during asymmetric division of Drosophila muscle progenitor cells, Inscuteable and Numb are segregated to the apical and basal sibling cells respectively (Carmena et al., 1998). Overexpression or knockdown either component leads to the failure of cell fate segregation and the formation of identical daughter cells (Carmena et al., 1998).

The identification of a satellite stem cell as described herein represents an important advance in our understanding of satellite cell biology and opens new avenues to explore for the treatment of degenerative neuromuscular diseases. For example, but not wishing to be bound by theory, such satellite stem cells may be used for direct transplantation into diseased muscle. Alternatively, understanding the molecular regulation of satellite stem cell symmetric versus asymmetric cell division will lead to identification of biologics or small drugs that specifically target the relevant pathway leading to satellite stem cell expansion.

Additional embodiments of the present invention are illustrated in the figures as provided herein.

The above description is not intended to limit the claimed invention in any manner, furthermore, the discussed combination of features might not be absolutely necessary for the inventive solution.

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Armand O, Boutineau A M, Mauger A, et al. 1983. Origin of satellite cells in avian skeletal muscles. Arch Anat Microsc Morphol Exp 72, 163-181.

Asakura A, Seale P, Girgis-Gabardo A, et al. 2002. Myogenic specification of side population cells in skeletal muscle. J Cell Biol 159, 123-134.

Beauchamp J R, Heslop L, Yu D S, et al. 2000. Expression of CD34 and myf5 defines the majority of quiescent adult skeletal muscle satellite cells [In Process Citation]. J Cell Biol 151, 1221-1234.

Beauchamp J R, Morgan J E, Pagel C N, et al. 1999. Dynamics of myoblast transplantation reveal a discrete minority of precursors with stem cell-like properties as the myogenic source. J Cell Biol 144, 1113-1122.

Ben-Yair R, Kalcheim C. 2005. Lineage analysis of the avian dermomyotome sheet reveals the existence of single cells with both dermal and muscle progenitor fates. Development 132, 689-701.

Bischoff R 1994. The satellite cell and muscle regneration. In Myology, A. G. Engel, and C. Franzini-Armstrong, eds. (New York, McGraw-Hill), pp. 97-118.

Blanco-Bose W E, Yao C C, Kramer R H, et al. 2001. Purification of mouse primary myoblasts based on alpha 7 integrin expression. Exp Cell Res 265, 212-220.

Bornemann A, Schmalbruch H. 1994. Immunocytochemistry of M-cadherin in mature and regenerating rat muscle. Anat Rec 239, 119-125.

Burkin D J, Kaufman S J. 1999. The alpha7beta1 integrin in muscle development and disease. Cell Tissue Res 296, 183-190.

Carmena A, Murugasu-Oei B, Menon D, et al. 1998. Inscuteable and numb mediate asymmetric muscle progenitor cell divisions during Drosophila myogenesis. Genes Dev 12, 304-315.

Charge S B, Rudnicki M A. 2004. Cellular and molecular regulation of muscle regeneration. Physiological reviews in press.

Collins C A. 2006. Satellite cell self-renewal. Curr Opin Pharmacol. Collins C A, Olsen I, Zammit P S, et al. 2005. Stem cell function, self-renewal, and behavioral heterogeneity of cells from the adult muscle satellite cell niche. Cell 122, 289-301.

Collo G, Starr L, Quaranta V. 1993. A new isoform of the laminin receptor integrin alpha 7 beta 1 is developmentally regulated in skeletal muscle. J Biol Chem 268, 19019-19024.

Conboy I M, Rando T A. 2002. The regulation of Notch signaling controls satellite cell activation and cell fate determination in postnatal myogenesis. Dev Cell 3, 397-409.

Cornelison D D, Filla M S, Stanley H M, et al. 2001. Syndecan-3 and syndecan-4 specifically mark skeletal muscle satellite cells and are implicated in satellite cell maintenance and muscle regeneration. Dev Biol 239, 79-94.

Cornelison D D, Wold B J. 1997. Single-cell analysis of regulatory gene expression in quiescent and activated mouse skeletal muscle satellite cells. Dev Biol 191, 270-283.

Cousins J C, Woodward K J, Gross J G, et al. 2004. Regeneration of skeletal muscle from transplanted immortalised myoblasts is oligoclonal. J Cell Sci 117, 3259-3269.

De Angelis L, Berghella L, Coletta M, et al. 1999. Skeletal myogenic progenitors originating from embryonic dorsal aorta coexpress endothelial and myogenic markers and contribute to postnatal muscle growth and regeneration. J Cell Biol 147, 869-878.

Delfini M, Hirsinger E, Pourquie O, et al. 2000. Delta 1-activated notch inhibits muscle differentiation without affecting Myf5 and Pax3 expression in chick limb myogenesis. Development 127, 5213-5224.

Dhawan J, Rando T A. 2005. Stem cells in postnatal myogenesis: molecular mechanisms of satellite cell quiescence, activation and replenishment. Trends Cell Biol 15, 666-673.

El Fahime E, Bouchentouf M, Benabdallah B F, et al. 2003. Tubulyzine, a novel trisubstituted triazine, prevents the early cell death of transplanted myogenic cells and improves transplantation success. Biochem Cell Biol 81, 81-90.

Fan Y, Maley M, Beilharz M, et al. 1996. Rapid death of injected myoblasts in myoblast transfer therapy. Muscle Nerve 19, 853-860.

Fuchs E, Tumbar T, Guasch G. 2004. Socializing with the neighbors: stem cells and their niche. Cell 116, 769-778.

Garry D J, Yang Q, Bassel-Duby R, et al. 1997. Persistent expression of MNF identifies myogenic stem cells in postnatal muscles. Dev Biol 188, 280-294.

Gros J, Manceau M, Thome V, et al. 2005. A common somitic origin for embryonic muscle progenitors and satellite cells. Nature 435, 954-958.

Heslop L, Beauchamp J R, Tajbakhsh S, et al. 2001. Transplanted primary neonatal myoblasts can give rise to functional satellite cells as identified using the Myf5nlacZ1+ mouse. Gene Ther 8, 778-783.

Heslop L, Morgan J E, Partridge T A. 2000. Evidence for a myogenic stem cell that is exhausted in dystrophic muscle. J Cell Sci 113, 2299-2308.

Hodgetts S I, Beilharz M W, Scalzo A A, et al. 2000. Why do cultured transplanted myoblasts die in vivo? DNA quantification shows enhanced survival of donor male myoblasts in host mice depleted of CD4+ and CD8+ cells or Nk1.1+ cells. Cell Transplant 9, 489-502.

Holowacz T, Zeng L, Lassar A B. 2006. Asymmetric localization of numb in the chick somite and the influence of myogenic signals. Dev Dyn 235, 633-645.

Irintchev A, Zeschnigk M, Starzinski-Powitz A, et al. 1994. Expression pattern of Mcadherin in normal, denervated, and regenerating mouse muscles. Dev Dyn 199, 326-337.

Kassar-Duchossoy L, Giacone E, Gayraud-Morel B, et al. 2005. Pax3/Pax7 mark a novel population of primitive myogenic cells during development. Genes Dev 19, 1426-1431.

Kinoshita I, Vilquin J T, Guerette B, et al. 1994. Immunosuppression with FK 506 insures good success of myoblast transplantation in MDX mice. Transplant Proc 26, 3518.

Kuang S, Charge S B, Seale P, et al. 2006. Distinct roles for Pax7 and Pax3 in adult regenerative myogenesis. J Cell Biol 172, 103-113.

LaBarge M A, Blau H M. 2002. Biological progression from adult bone marrow to mononucleate muscle stem cell to multinucleate muscle fiber in response to injury. Cell 111, 589-601.

Lechler T, Fuchs E. 2005. Asymmetric cell divisions promote stratification and differentiation of mammalian skin. Nature 437, 275-280.

Mauro A. 1961. Satellite cells of skeletal muscle fibres. J Biophy Biochem Cytol 9, 493-495.

Megeney L A, Kablar B, Garrett K, et al. 1996. MyoD is required for myogenic stem cell function in adult skeletal muscle. Genes Dev 10, 1173-1183.

Minoguchi S, Taniguchi Y, Kato H, et al. 1997. RBP-L, a transcription factor related to RBP-Jkappa. Mol Cell Biol 17, 2679-2687.

Montarras D, Morgan J, Collins C, et al. 2005. Direct isolation of satellite cells for skeletal muscle regeneration. Science 309, 2064-2067.

Olguin H C, Olwin B B. 2004. Pax-7 up-regulation inhibits myogenesis and cell cycle progression in satellite cells: a potential mechanism for self-renewal. Dev Biol 275, 375-388.

Oustanina S, Hause G, Braun T. 2004. Pax7 directs postnatal renewal and propagation of myogenic satellite cells but not their specification. Embo J 23, 3430-3439.

Polesskaya A, Seale P, Rudnicki M A. 2003. Wnt Signaling Activates the Myogenic Recruitment of CD45+Adult Stem Cells during Muscle Regeneration. Dev Cell in press.

Qu Z, Balkir L, van Deutekom J C, et al. 1998. Development of approaches to improve cell survival in myoblast transfer therapy. J Cell Biol 142, 1257-1267.

Rando T A, Blau H M. 1994. Primary mouse myoblast purification, characterization, and transplantation for cell-mediated gene therapy. J Cell Biol 125, 1275-1287.

Relaix F, Montarras D, Zaffran S, et al. 2006. Pax3 and Pax7 have distinct and overlapping functions in adult muscle progenitor cells. J Cell Biol 172, 91-102.

Relaix F, Rocancourt D, Mansouri A, et al. 2005. A Pax3/Pax7-dependent population of skeletal muscle progenitor cells. Nature 435, 948-953.

Rosen G D, Sanes J R, LaChance R, et al. 1992. Roles for the integrin VLA-4 and its counter receptor VCAM-1 in myogenesis. Cell 69, 1107-1119.

Rosenblatt J D, Lunt A I, Parry D J, et al. 1995. Culturing satellite cells from living single muscle fiber explants. In Vitro Cell Dev Biol 31, 773-779.

Schienda J, Engleka K A, Jun S, et al. 2006. Somitic origin of limb muscle satellite and side population cells. Proc Natl Acad Sci USA 103, 945-950.

Schultz E. 1996. Satellite cell proliferative compartments in growing skeletal muscles. Dev Biol 175, 84-94.

Seale P, Sabourin L A, Girgis-Gabardo A, et al. 2000. Pax7 is required for the specification of myogenic satellite cells. Cell 102, 777-786.

Srinivas S, Watanabe T, Lin C S, et al. 2001. Cre reporter strains produced by targeted insertion of EYFP and ECFP into the ROSA26 locus. BMC Dev Biol 1, 4.

Tajbakhsh S, Bober E, Babinet C, et al. 1996. Gene targeting the myf-5 locus with nlacZ reveals expression of this myogenic factor in mature skeletal muscle fibres as well as early embryonic muscle. Dev Dyn 206, 291-300.

Tallquist M D, Weismann K E, Hellstrom M, et al. 2000. Early myotome specification regulates PDGFA expression and axial skeleton development. Development 127, 5059-5070.

Venters S J, Ordahl C P. 2005. Asymmetric cell divisions are concentrated in the dermomyotome dorsomedial lip during epaxial primary myotome morphogenesis. Anat Embryol (Berl) 209, 449-460.

Yablonka-Reuveni Z, Anderson J E. 2006. Satellite cells from dystrophic (mdx) mice display accelerated differentiation in primary cultures and in isolated myofibers. Dev Dyn 235, 203-212.

Zammit P S, Golding J P, Nagata Y, et al. 2004. Muscle satellite cells adopt divergent fates: a mechanism for self-renewal? J Cell Biol 166, 347-357.

Zammit P S, Relaix F, Nagata Y, et al. 2006. Pax7 and myogenic progression in skeletal muscle satellite cells. J Cell Sci.

---

The embodiments of the invention in which an exclusive property of privilege is claimed are defind as follows:

1. An isolated adult pax7+/Myf5-skeletal muscle satellite stem cell.

2. The cell of claim 1 further comprising one or more of the following markers: α-7 integrin, β-1 integrin, CD34, Syn 4, or N-CAM.

3. The isolated cell of claim 1 transformed with a heterologous nucleotide sequence of interest.

4. A composition comprising the isolated cell of claim 1 and one or more of the following: a) a cell culture or growth medium; b) a cryopreservation medium; c) a pharmaceutically acceptable delivery medium, or d) a combination thereof wherein the ratio of adult pax7+/Myf5- skeletal muscle satellite stem cells to pax7+/Myf5+ progenitor cells in the composition is greater than about 1 to 10.

5. The isolated cell of claim 1 further comprising an α-7 integrin marker.

6. The isolated cell of claim 1 further comprising a β-1 integrin marker.

7. The isolated cell of claim 1 further comprising a CD34 marker.

8. The isolated cell of claim 1 further comprising a Syn 4 marker.

9. The isolated cell of claim 1 further comprising a N-CAM marker.

10. The composition of claim 4 further comprising a Pax7+/Myf5+ skeletal muscle progenitor cell.

11. The composition of claim 4 comprising the cell culture or growth medium.

12. The composition of claim 4 comprising the cryopreservation medium.

13. The composition of claim 4 comprising the pharmaceutically acceptable delivery medium.

* * * * *